US012337136B2

(12) United States Patent
Mounce et al.

(10) Patent No.: US 12,337,136 B2
(45) Date of Patent: Jun. 24, 2025

(54) DRUG DELIVERY DEVICE PACKAGING

(71) Applicant: AMGEN INC., Thousand Oaks, CA (US)

(72) Inventors: Ronnie Paul Mounce, Burbank, CA (US); Gonghao Wang, Thousand Oaks, CA (US); Austin Wanek, Thousand Oaks, CA (US); Katie Lucchesi, Thousand Oaks, CA (US); Brian Stonecipher, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 18/854,605

(22) PCT Filed: Apr. 12, 2023

(86) PCT No.: PCT/US2023/018229
§ 371 (c)(1),
(2) Date: Oct. 7, 2024

(87) PCT Pub. No.: WO2023/200822
PCT Pub. Date: Oct. 19, 2023

(65) Prior Publication Data
US 2025/0108159 A1     Apr. 3, 2025

Related U.S. Application Data

(60) Provisional application No. 63/438,702, filed on Jan. 12, 2023, provisional application No. 63/414,357, (Continued)

(51) Int. Cl.
*A61M 5/00*     (2006.01)
(52) U.S. Cl.
CPC .................................. *A61M 5/002* (2013.01)

(58) Field of Classification Search
CPC .... B65D 5/4212; B65D 5/4216; B65D 5/425; A61B 5/002
(Continued)

(56) References Cited

U.S. PATENT DOCUMENTS

2011/0290260 A1* 12/2011 Tomes ................ A61B 50/30
128/849
2016/0030368 A1   2/2016 Atkins, Jr. et al.
(Continued)

FOREIGN PATENT DOCUMENTS

DE          29920360 U1    11/2000
WO      WO-95/09579 A1    4/1995

OTHER PUBLICATIONS

International Search Report for Application No. PCT/US2023/018229 mailed Jul. 11, 2023.
(Continued)

*Primary Examiner* — Jacob K Ackun
(74) *Attorney, Agent, or Firm* — MARSHALL, GERSTEIN & BORUN LLP; Michael P. Furmanek

(57) ABSTRACT

Kits for a drug delivery device or system include a housing having compartments, components to be secured within the compartments, and an instruction manual providing a series of steps. In some kits, a page of the instruction manual providing a step associated with a component does not overlay the compartment in which the associated component is to be secured, whereas all preceding pages do overlay the compartment, such that the step and the associated component are first displayed together. In some kits, a color is displayed with a compartment and with a step associated with the component to be secured in the compartment. In some kits, the housing includes two chambers, each chamber
(Continued)

having the compartments in which components associated with a first subset of steps and a second subset of steps, respectively are secured.

11 Claims, 23 Drawing Sheets

Related U.S. Application Data filed on Oct. 7, 2022, provisional application No. 63/331,707, filed on Apr. 15, 2022.

(58) Field of Classification Search
USPC .................................. 206/570, 571, 459.5
See application file for complete search history.

(56) References Cited

U.S. PATENT DOCUMENTS

| | | | |
|---|---|---|---|
| 2017/0326290 A1 | 11/2017 | Dittrich | |
| 2020/0338259 A1* | 10/2020 | Mainz | A61B 50/30 |
| 2022/0387700 A1* | 12/2022 | Gibson | G06Q 20/12 |

OTHER PUBLICATIONS

Written Opinion for Application No. PCT/US2023/018229 mailed Jul. 11, 2023.
Morgan, Victoria, How Large-Volume Wearables are Revolutionising the Patient Experience, West Phamaceutical, Sep. 17, 2021 (Sep. 17, 2021), pp. 1-5. XPO55951459, Retrieved from the Internet: URL:https://www.ondrugdelivery.com/wpcontent/uploads/2019/09/1OO_2019_West.pdf.

* cited by examiner

DRUG DELIVERY DEVICE PACKAGING

CROSS-REFERENCE TO RELATED APPLICATION

This is the United States national phase of International Patent Application No. PCT/US2023/018229, filed Apr. 12, 2023, which claims priority to U.S. Provisional Patent Application No. 63/331,707, filed Apr. 15, 2022; U.S. Provisional Patent Application No. 63/414,357 filed Oct. 7, 2022; and U.S. Provisional Patent Application No. 63/438,702, filed Jan. 12, 2023, the entire contents of each of which are hereby incorporated by reference herein.

FIELD OF THE DISCLOSURE

The present disclosure relates to packaging for a drug delivery device or system, and specifically relates to packaging for a drug delivery device or system configured to facilitate assembly and administration of a drug by associating steps in an instruction manual with the relevant drug delivery device components used in the steps.

BACKGROUND

Some drugs must be administered by injection. Patients who must receive such drugs can avoid the inconvenience, time, and expense associated with having a medical professional administer the injection by performing the injection themselves. However, the process of assembling the drug delivery device and performing the injection can be daunting. The drug delivery device typically has many components that must be put together in a particular order. Sometimes multiple drug delivery devices that are part of a drug delivery system must be used, resulting in even more components that must be assembled properly. The instruction manual typically has many steps to follow. A user must accurately identify the correct component to use in each step, which can be challenging depending on the clarity of the instructions and the ease with which the component can be recognized while still packaged. Moreover, a user must maintain the sterility of various components to ensure a safe injection. Removing components from packaging in order to accurately identify them can result in disorganization and potential contamination prior to use. These challenges can discourage a patient who would prefer to perform an injection themselves from doing so.

SUMMARY

In accordance with an example, a kit for a drug delivery device or system includes a housing, a plurality of components, and an instruction manual. The housing has a plurality of compartments. Each component of the plurality of components is configured to be secured within a compartment of the plurality of compartments of the housing. The instruction manual has a plurality of pages connected to the housing along a binding axis and arranged in a progressive order. Each page of the plurality of pages is configured to rotate from a first position on a first side of the binding axis to a second position on a second side of the binding axis. A series of steps for using and/or assembling the drug delivery device or system is provided within the instruction manual. The series of steps includes component steps. Each component step is associated with at least one of the plurality of components. A plurality of component pages are included within the plurality of pages. Each component page displays a respective component step, and each component page is associated with a compartment of the plurality of compartments that is configured to secure the at least one of the plurality of components associated with the respective component step. Each component page is sized and configured to not overlay the associated compartment in the first position. All pages of the plurality of pages preceding a respective component page of the plurality of component pages in the progressive order are sized and configured to overlay the associated compartment of the respective component page in the first position such that the respective component page and the associated compartment are first displayed together to a user using the instruction manual in the progressive order.

In some forms, the binding axis may be positioned such that the first position of each page is to the right of the second position of each page.

In some forms, the plurality of compartments may be positioned such that a user using the instruction manual in the progressive order will reveal the plurality of compartments in a sequential order from a top of the housing to a bottom of the housing. The sequential order may reveal compartments of the plurality of compartments that are at a substantially similar position between the top of the housing and the bottom of the housing in a secondary sequential order from left to right.

In some forms, the housing may include a box, a tray positioned within the box, and a protective cover rotatably secured to the box. The tray may include at least one channel positioned adjacent at least one compartment of the plurality of compartments to facilitate picking up at least one component of the plurality of components. In some forms, the protective cover may be connected to the box at a hinge along the left side of the box and the instruction manual may be connected to the box along the hinge. In other forms, the instruction manual may be connected to a top surface of the tray.

In some forms, the housing may include a box, a tray positioned within the box, and a protective cover rotatably secured to the box. A compartment of the plurality of compartments may include a form fitting recess within the tray for one of the components of the plurality of components. The housing may further include a panel with tuck flaps configured to be secured over the tray. The instruction manual may be connected to the tray by binding tabs.

In accordance with an example, a kit for a drug delivery device or system includes a housing, a plurality of components, and an instruction manual. The housing has a plurality of compartments. Each component of the plurality of components is configured to be secured within a compartment of the plurality of compartments of the housing. The instruction manual has a plurality of pages. A series of steps for using and/or assembling the drug delivery device or system is provided within the instruction manual. The series of steps include component steps. Each component step is associated with at least one of the plurality of components and the compartment of the plurality of compartments in which the associated at least one of the plurality of components is configured to be secured. A color is displayed with a respective compartment of the plurality of compartments, and the color is also displayed with a respective component step associated with the respective compartment. The color is configured to direct a user reading the respective component step to the associated at least one of the plurality of components.

In some forms, the series of steps may include a first subset of steps and a second subset of steps. Each component step may be assigned to either the first subset or the second subset. The color may be a first color displayed with component steps assigned to the first subset and compartments associated with the component steps assigned to the first subset. A second color may be displayed with component steps assigned to the second subset and compartments associated with the component steps assigned to the second subset.

In some forms, a unique color may be displayed with each component step and the compartment associated therewith.

In some forms, the housing may include a base comprising the plurality of compartments and a cover connected to the base at a hinge. The instruction manual may be connected to the cover, and the cover may be configured to cover the plurality of compartments in a first orientation and configured to hold the instruction manual upright in a second orientation.

In accordance with an example, a kit for a drug delivery device or system includes a housing, a plurality of components, and an instruction manual. The housing has a plurality of compartments, and each compartment is positioned within a first chamber or a second chamber. Each component of the plurality of components is configured to be secured within a compartment of the plurality of compartments of the housing. The instruction manual has a plurality of pages. A series of steps for using and/or assembling the drug delivery device or system is provided on the plurality of pages. The series of steps include a first subset of steps, a second subset of steps, and component steps. Each component step is assigned to either the first subset or the second subset. Each component step is associated with a respective at least one of the plurality of components and with a respective compartment of the plurality of compartments configured to secure the respective at least one of the plurality of components. The first chamber includes each respective compartment associated with each component step assigned to the first subset of steps. The second chamber includes each respective compartment associated with each component step assigned to the second subset of steps.

In some forms, the first chamber and the second chamber may be sealed separately from one another.

In some forms, the housing may have a central instruction surface on which the instruction manual is disposed. The first chamber may be hingedly connected to the central instruction surface on a first side. The second chamber may be hingedly connected to the central instruction surface on a second side. The housing may be configured to transition between an open configuration where the plurality of compartments are accessible for use and a closed configuration where the first chamber and the second chamber are each rotated relative to the central instruction surface and connected to one another to prevent access to the plurality of compartments.

In some forms, the housing may include a first tray including the first chamber and a second tray including the second chamber. The first tray may be stackable on the second tray.

In some forms, the housing may include a box and a tray disposed within the box. The tray may include the first chamber and the second chamber. A protective cover may be rotatably secured to the box. The first chamber may include at least one channel positioned adjacent at least one compartment of the plurality of compartments to facilitate picking up at least one component of the plurality of components.

In some forms, the housing may include a box, a tray disposed within the box, and a protective cover rotatably secured to the box. The tray may include the first chamber and the second chamber. Each compartment positioned within the first chamber may be defined by a form fitting recess.

BRIEF DESCRIPTION OF THE DRAWINGS

The figures described herein depict various aspects of the system and methods disclosed herein. It should be understood that each figure depicts an example of aspects of the present systems and methods.

Figure 1:
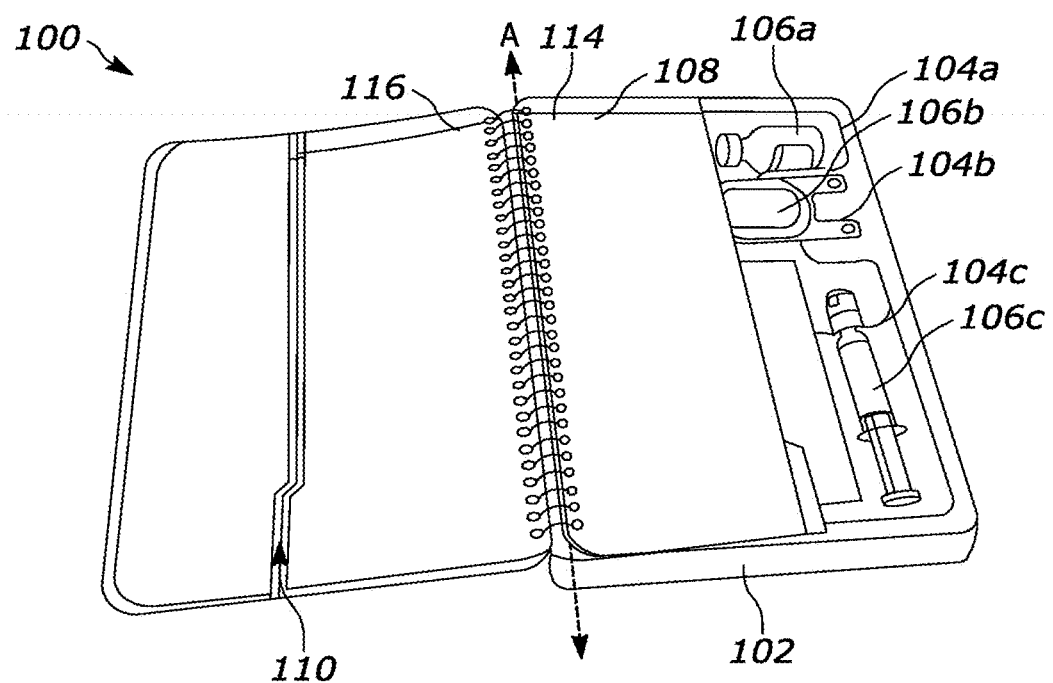
FIG. 1 is a perspective view of a first arrangement illustrating progressive display drug delivery packaging.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various examples. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

The disclosed drug delivery device and system packaging kits allow a user to easily identify a component of a drug delivery device or system referenced by a step of an instruction manual while the component is still located in the packaging. This reduces stress and uncertainty on the part of a user, expedites the process of assembling the drug delivery device or system, and helps to maintain the sterility of the components of the drug delivery device or system. One method by which various kits disclosed herein facilitate identification of components is by securing an instruction manual over compartments for the various components and then configuring the size and shape of pages of the instruction manual to first display a relevant component at the time that the component is first introduced in a step described in the instruction manual. Because a component is not visible to a user until the user reaches the step where it is needed, the user is effectively prevented from accessing a component too soon. Another method by which various kits disclosed herein facilitate identification of components is by coordinating colors displayed with a step in the instruction manual and with a compartment for a component used in the step. A user intuitively grasps that the same color should be used with the step and the component used in the step, and the colors thereby clarify for a user whether they have identified the correct component. Yet another method by which various kits disclosed herein facilitate identification of components is by locating each compartment in one of two chambers, a first chamber associated with a first subset of steps in the instruction manual and a second chamber associated with a second subset of steps in the instruction manual. For example, an injection process may include steps for reconstituting a drug (i.e., a first subset of steps) and steps for injecting the drug (i.e., a second subset of steps). By having the respective components divided into two chambers, a user understands to look only to the chamber for the particular part of the injection process they are executing, thereby reducing the number of compartments that a user must review to identify the correct compartment securing the correct component. These three methods may be used alone in a kit or may be combined to assist a user in multiple ways.

Progressive Display Drug Delivery Packaging

Figure 3:
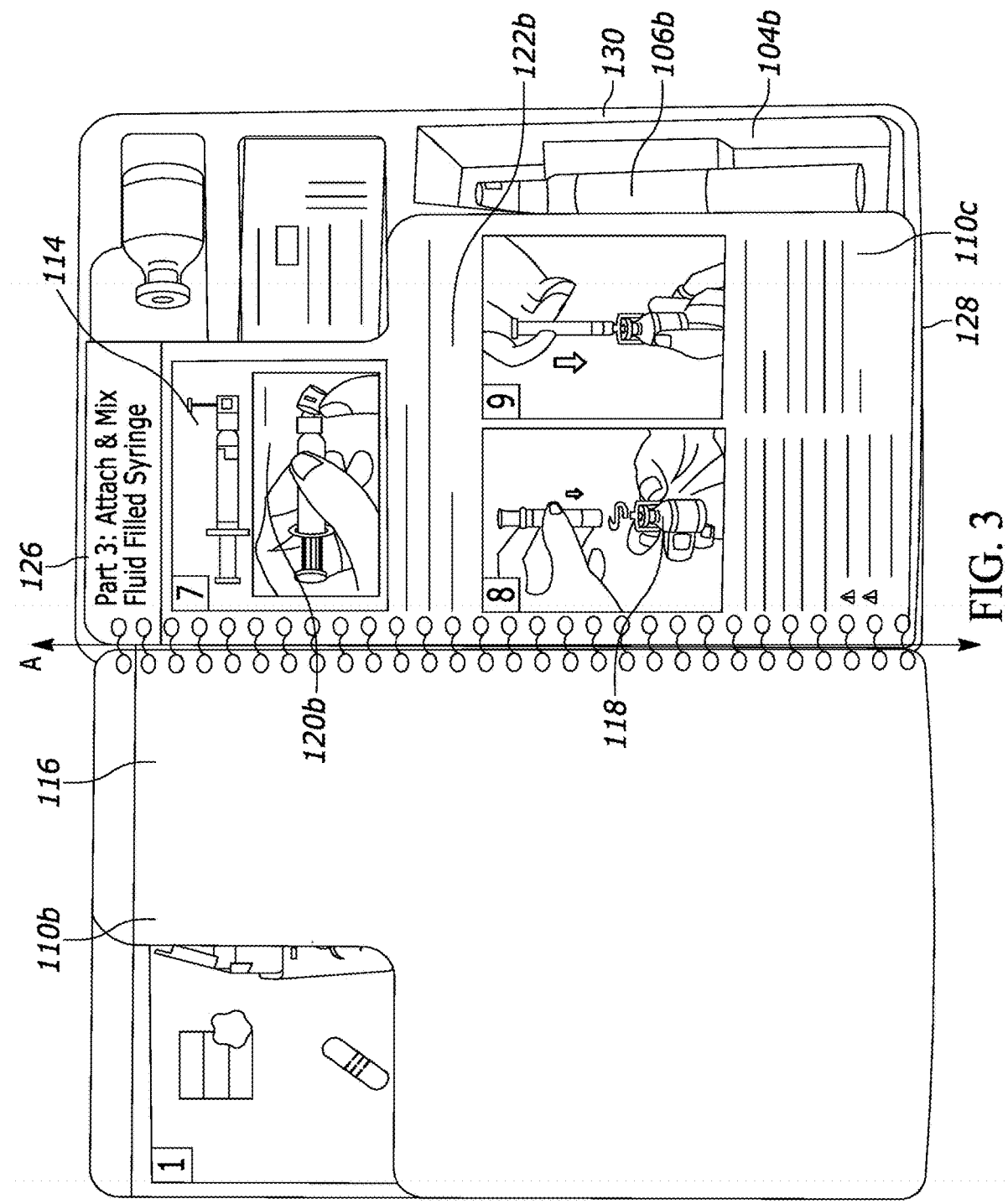
FIG. 3 is a top view of the first arrangement of FIGS. 1 and 2 illustrating a reveal of a component used subsequent to the first component alongside instructions for its use.
Figure 4:
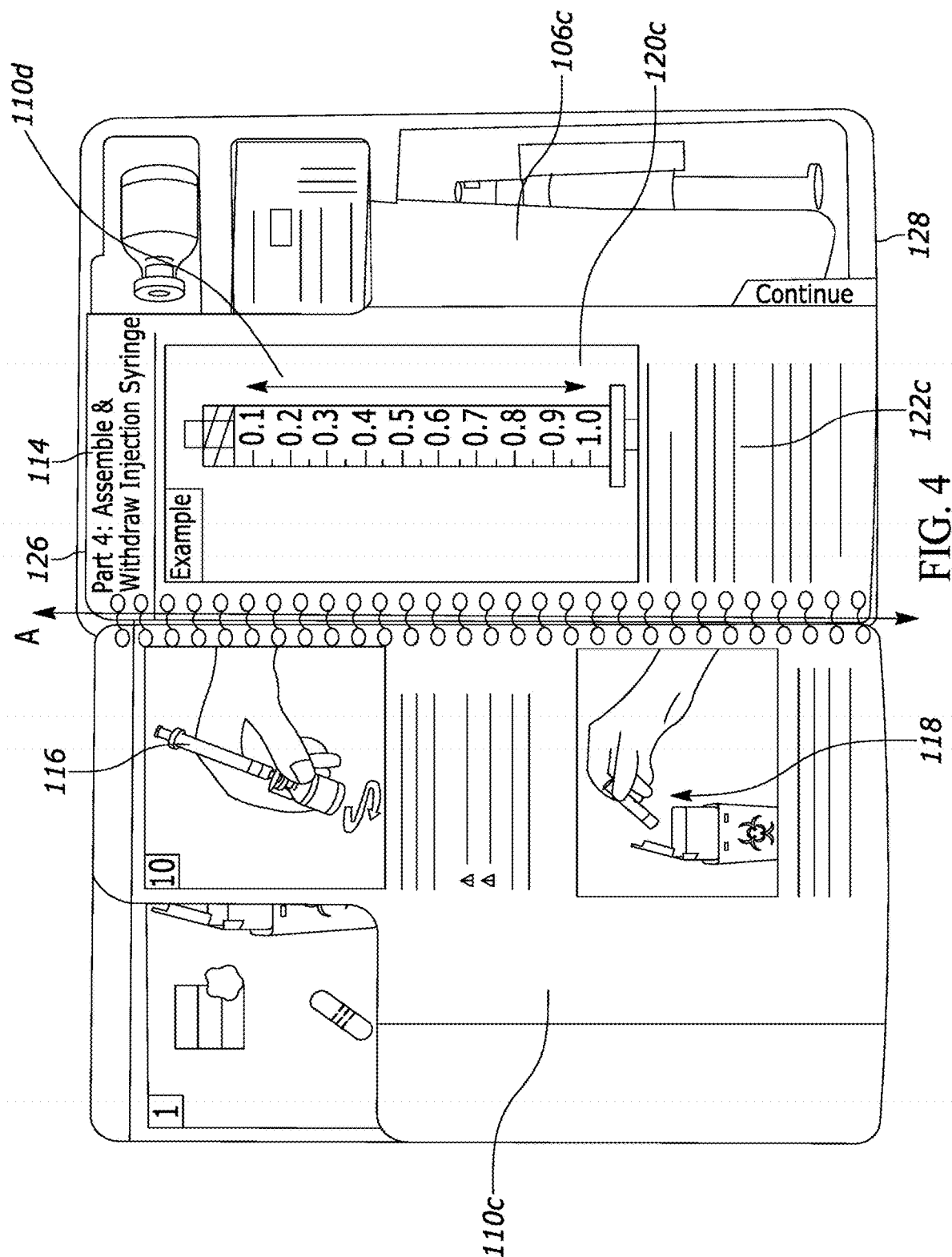
FIG. 4 is a top view of the first arrangement of FIGS. 1-3 illustrating a reveal of a component used subsequent to the components revealed in FIGS. 2 and 3.
Figure 5:
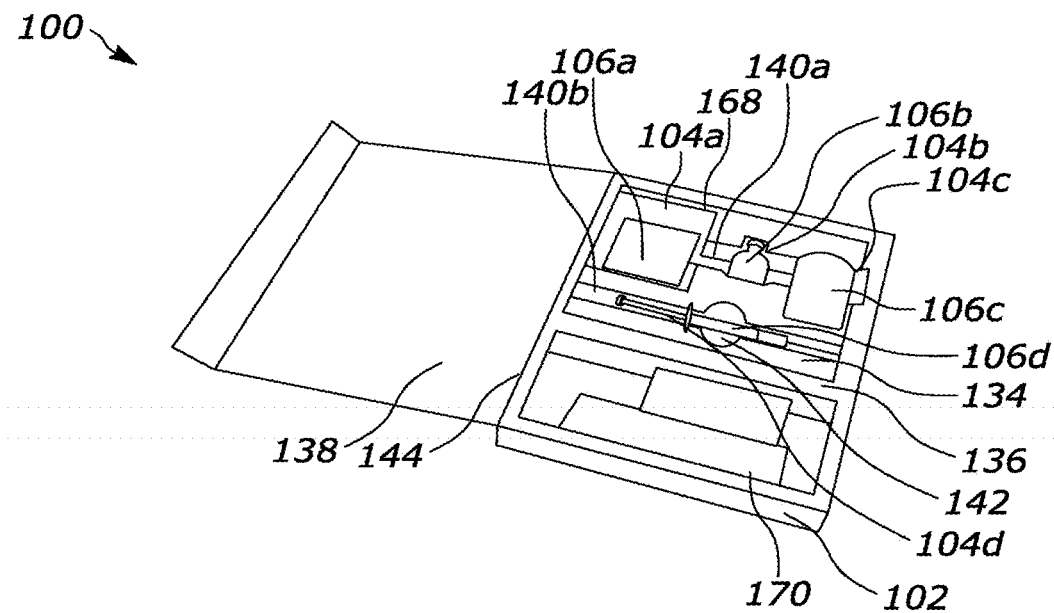
FIG. 5 is a perspective view of a second arrangement illustrating progressive display drug delivery packaging having a top-down paperboard tray.
Figure 6:
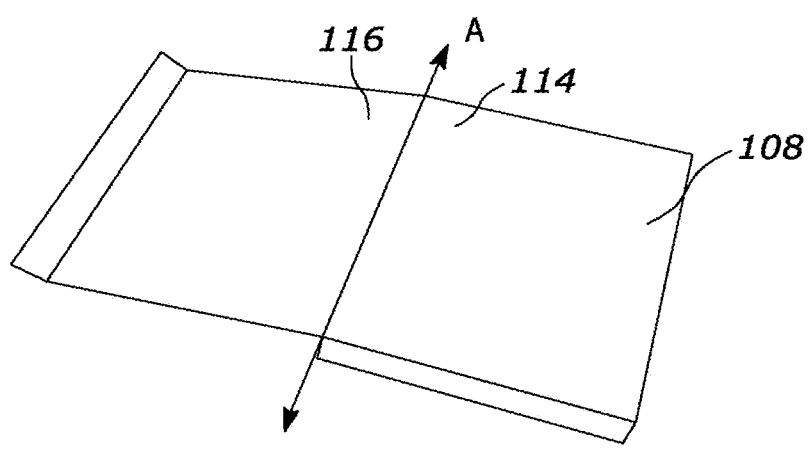
FIG. 6 is a perspective view of the second arrangement of FIG. 5 illustrating placement of an instruction manual.
Figure 7:
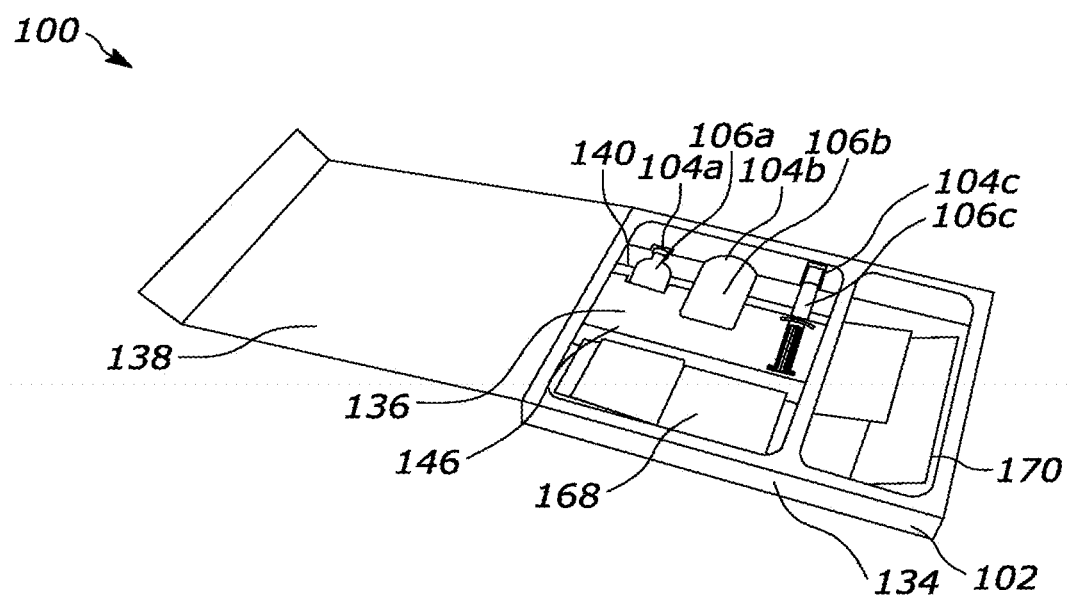
FIG. 7 is a perspective view of a third arrangement illustrating progressive display drug delivery packaging having a left-to-right paperboard tray.
Figure 8:
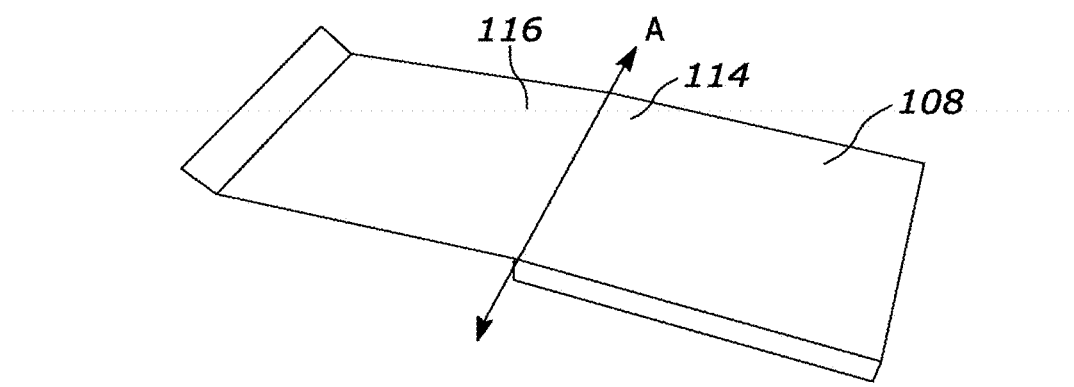
FIG. 8 is a perspective view of the third arrangement of FIG. 7 illustrating placement of an instruction manual.
Figure 9:
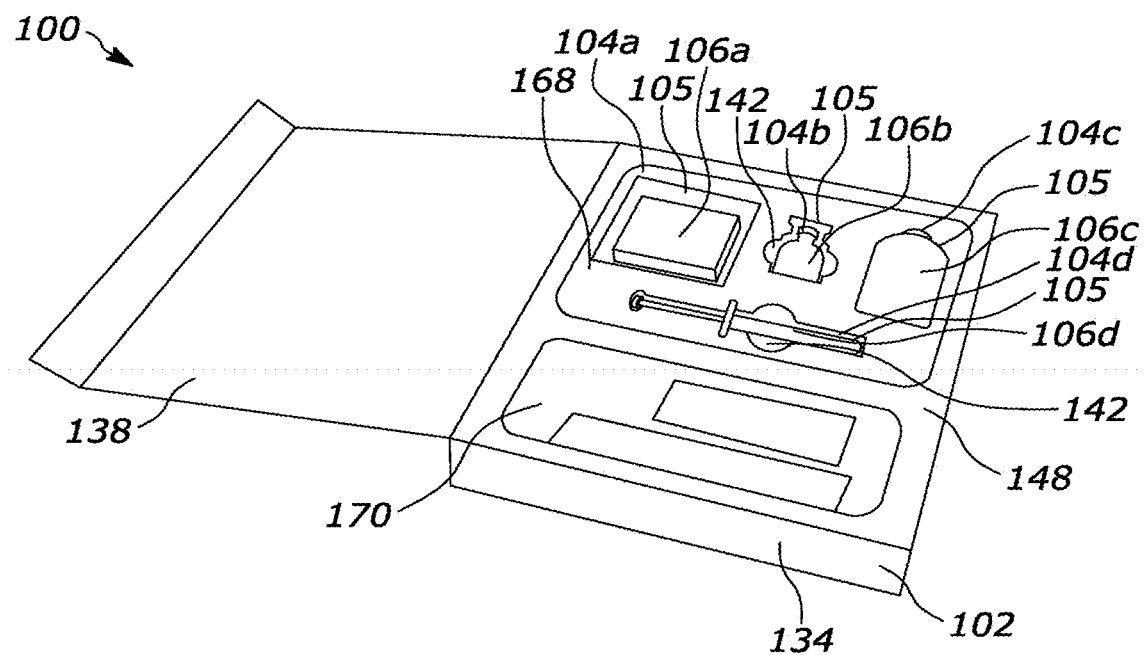
FIG. 9 is a perspective view of a fourth arrangement illustrating progressive display drug delivery packaging having a top-down rPET tray.
Figure 10:
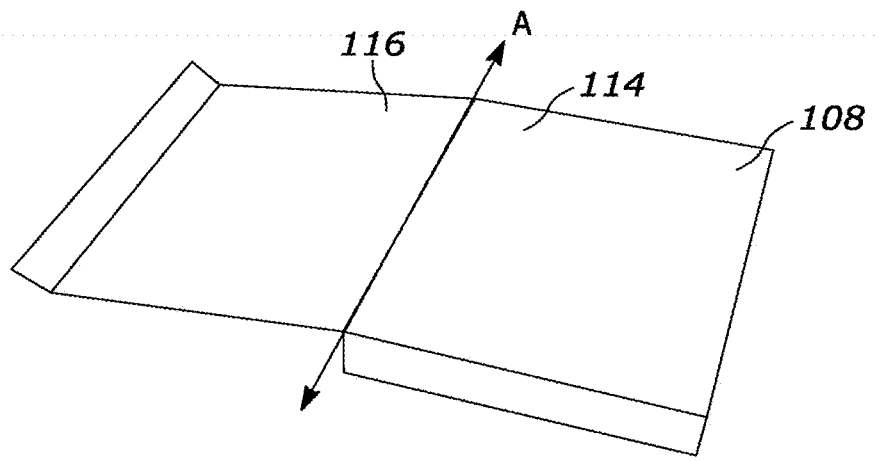
FIG. 10 is a perspective view of the fourth arrangement of FIG. 9 illustrating placement of an instruction manual.
Figure 11:
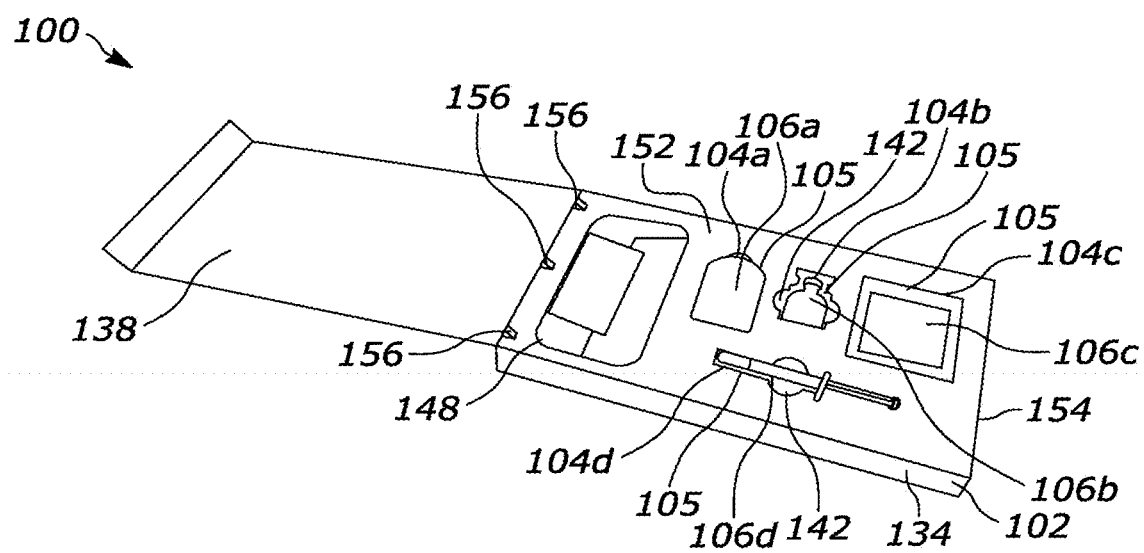
FIG. 11 is a perspective view of a fifth arrangement illustrating progressive display drug delivery packaging having a left-to-right paperboard tray.
Figure 12:
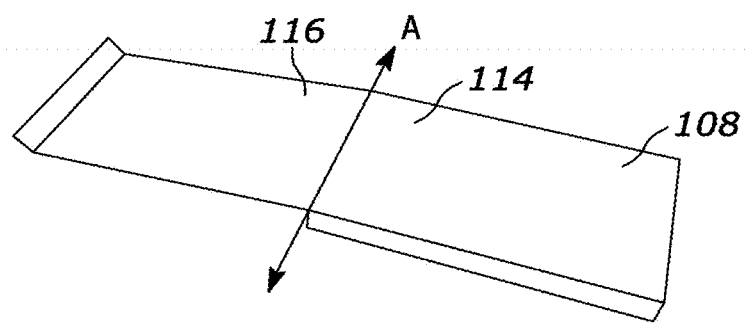
FIG. 12 is a perspective view of the fifth arrangement of FIG. 11 illustrating placement of an instruction manual.

Five arrangements of drug delivery device packaging kits 100 are disclosed in FIGS. 1-12, each illustrating the progressive display method discussed above. A first arrangement of drug delivery packaging is shown in FIGS. 1-4. A second arrangement of drug delivery packaging is shown in FIGS. 5-6. A third arrangement of drug delivery packaging is shown in FIGS. 7-8. A fourth arrangement of drug delivery packaging is shown in FIGS. 9-10. A fifth arrangement of drug delivery packaging is shown in FIGS. 11-12. Common features in each of the first, second, third, fourth, and fifth arrangements are identified by the same reference number. After their initial introduction, common features are not described in substantial detail for subsequent arrangements. Unique features are identified by unique reference numbers. Any combination or sub-combination of features described in regard to the first, second, third, fourth, and fifth arrangements may be incorporated into another of the first, second, third, fourth, and fifth arrangements, and vice-versa.

While each of the drug delivery packaging kits 100 shown in the first, second, third, fourth, and fifth arrangements are directed to packaging for a single drug delivery device, the drug delivery packaging kits 100 could also be used for a drug delivery system including multiple drug delivery devices. A drug delivery packaging kit 100 for a drug delivery system would operate according to the same principles described below but assembly of the components contained within the drug delivery packaging kit 100 according to the instructions provided therein would result in the assembly of multiple drug delivery devices instead of just one drug delivery device.

Starting with the first arrangement of FIGS. 1-4, a kit 100 for a drug delivery device includes a housing 102 having a plurality of compartments 104 (104a, 104b, 104c . . . ). The kit 100 includes a plurality of components 106 (106a, 106b, 106c . . . ) of the drug delivery device. For example, the plurality of components 106 may include an injection syringe, a product vial, an injection needle, a plunger rod, sterile water, a fluid filled syringe, a vial adaptor, or other products needed for assembly of the drug delivery device and administration of the injection. Each component (106a, 106b, 106c . . . ) of the plurality of components 106 is configured to be secured within a compartment (104a, 104b, 104c . . . ) of the plurality of compartments 104 of the housing 102, typically by a friction fit. In some arrangements, a single component (e.g., 106a) may be secured in a single compartment (e.g., 104a). In other arrangements, multiple components (e.g., 106a and 106b) may be secured within a single compartment (e.g., 104a), particularly if the multiple components will be first used simultaneously (e.g., a sterilizing wipe and a syringe).

As shown in the first arrangement of FIGS. 1-4, the kit 100 includes an instruction manual 108 having a plurality of pages 110 (110a, 110b, 110c . . . ) connected to the housing 102 along a binding axis A. The pages are arranged in a progressive order—for example, page 110a in FIG. 2, page 110b in FIG. 3, and page 110c in FIG. 4. Each page (110a, 110b, 110c . . . ) is configured to rotate from a first position on a first side 114 of the binding axis A to a second position on a second side 116 of the binding axis A. A series of steps 118 for using the drug delivery device are provided within the instruction manual 108. The series of steps 118 including component steps 120 (120a, 120b, 120c), each component step (120a, 120b, 120c) associated with at least one of the plurality of components 106 (106a, 106b, 106c . . . ).

Figure 2:
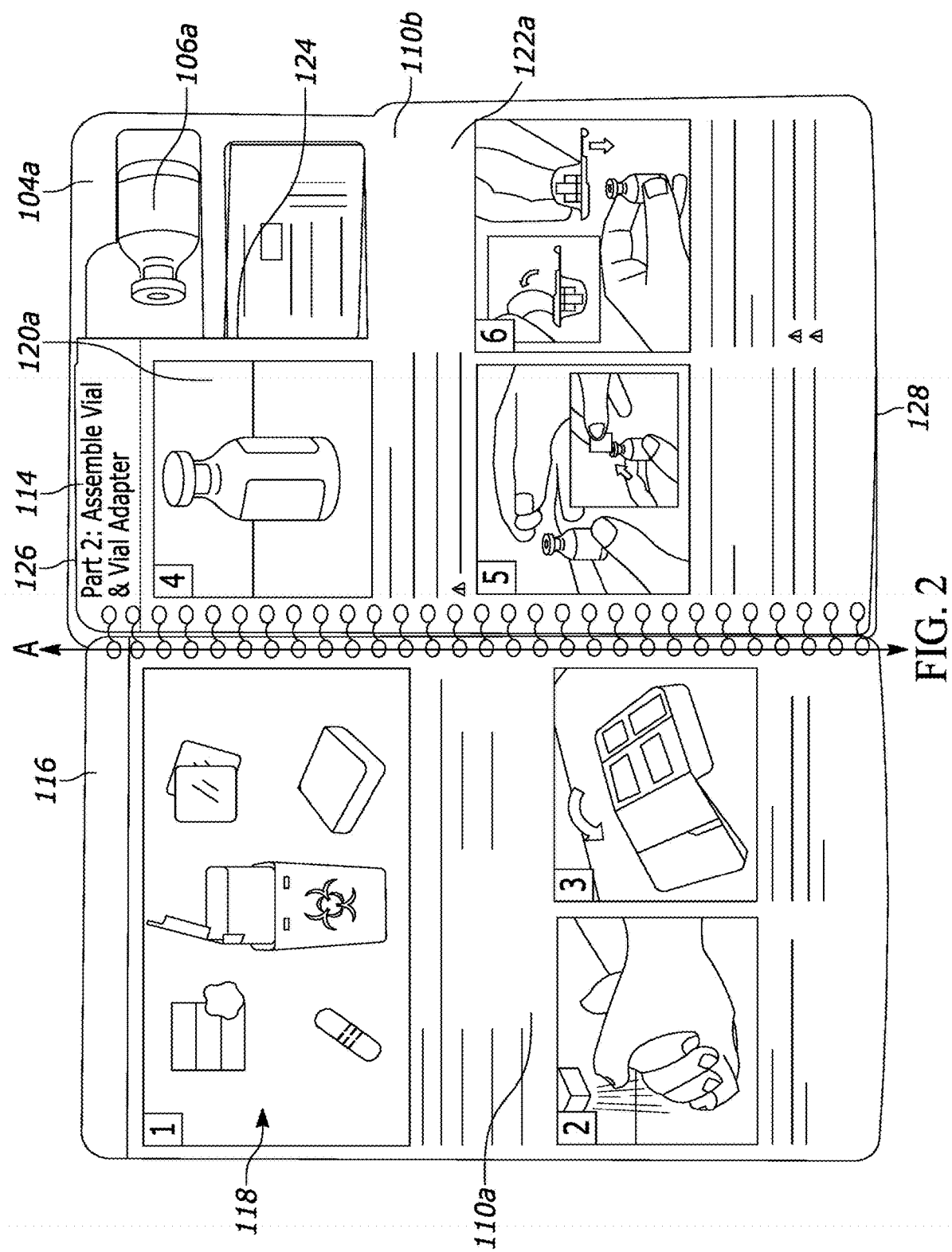
FIG. 2 is a top view of the first arrangement FIG. 1 illustrating a reveal of a first component alongside instructions for its use.

A plurality of component pages 122 (122a, 122b, 122c . . . ) are included within the plurality of pages 110. As shown in FIGS. 2-4, each component page (122a, 122b, 122c . . . ) displays a respective component step (120a, 120b, 120c . . . ). Each component page (122a, 122b, 122c . . . ) is associated with a compartment (104a, 104b, 104c . . . ) of the plurality of compartments 104 that is configured to secure the at least one of the plurality of components (106a, 106b, 106c . . . ) associated with the respective component step (120a, 120b, 120c). Each component page (122a, 122b, 122c . . . ) is sized and configured to not overlay the associated compartment (104a, 104b, 104c . . . ) in the first position.

For example, FIG. 2 shows page 110a and 110b of the instruction manual 108. Page 110a displays three steps 118, and page 110b displays three steps 118. One of the three steps on page 110b is a component step 120a because it introduces a component 106a—specifically, the product vial. Accordingly, the component step 120a is associated with the component 106a (i.e., the product vial). Because page 110b displays the component step 120a, page 110b is a component page 122a. The component page 122a is associated with the compartment 104a that is configured to secure the component 106a (i.e., the product vial) associated with the component step 120a that is displayed thereon. In the first position (i.e., when the component page 122a is on the first side 114 of the binding axis A), the component page 122a does not overlay the associated compartment 104a. As a result, a user reading the component step 120a on component page 122a can see the component 106a (i.e., the product vial) within its compartment 104a. Specifically, the component page 122a has a cutout area 124 disposed over the compartment 104a associated with it.

All pages of the plurality of pages 110 preceding a respective component page (122a, 122b, 122c . . . ) of the plurality of component pages 122 in the progressive order are sized and configured to overlay the associated compartment (104a, 104b, 104c . . . ) of the respective component page (122a, 122b, 122c . . . ) in the first position such that the respective component page (122a, 122b, 122c . . . ) and the associated compartment (104a, 104b, 104c . . . ) are first displayed together to a user using the instruction manual in the progressive order. For example, page 110b is shown in the first position in FIG. 2. In FIG. 3, page 110b is shown in the second position and new page 110c of the instruction manual 108 is visible in the first position. Page 110b precedes page 110c in the progressive order. Page 110c is a component page 122b because it displays a component step 120b that introduces a component 106b—specifically, a fluid-filled syringe. Accordingly, as shown in FIG. 3, component page 122b does not overlay the compartment 104b that is configured to secure the component 106b (i.e., the fluid-filled syringe) associated with the component step 120b that is displayed thereon. However, as shown in FIG. 2, page 110b does overlay the compartment 104b associated with the component page 122b when page 110b is in the first position. Accordingly, the component page 122b and the associated compartment 104b are first displayed to a user using the instruction manual in the progressive order, and the component 106b is also first displayed with the component page 122b to the user using the instruction manual in the progressive order when the component 106b is in the compartment 104b. Because the component 106b is covered by page 110b (and pages preceding it in the progressive order) up until it is needed in conjunction with component step 120b, a user is unlikely to mistakenly use the component 106b before it is needed and is able to easily identify component 106b at a proper time during use of the instruction manual 108. This process repeats when page 110c is turned to the second position in FIG. 4, where page 110d is a component page 122c displaying component step 120c and associated with compartment 104c for component 106c (i.e., the injection syringe).

All of the first through fifth arrangements (FIGS. 1-12) have the binding axis A positioned relative to the housing 102 such that the first position of each page (110a, 110b, 110c) is to the right of the second position of each page (110a, 110b, 110c). That is, the first position on the first side 114 of the binding axis A is the right of the binding axis A, while the second position on the second side 114 of the binding axis A is to the left of the binding axis A. However, in other arrangements, the binding axis A may be positioned relative to the housing 102 such that a first position of each page (110a, 110b, 110c) is either below or above a second position of each page (110a, 110b, 110c).

In all of the first through fifth arrangements (FIGS. 1-12), the plurality of compartments 104 are positioned such that a user using the instruction manual 108 in the progressive order will reveal the plurality of compartments 104 in a sequential order from a top 126 of the housing 102 to a bottom 128 of the housing 102. For example, comparing FIG. 2 and FIG. 3, the component page 122a precedes component page 122b, and the compartment 104a associated with the component page 122a is located closer to the top 126 of the housing 102 than the compartment 104b associated with the component page 122b. In the arrangement shown with the first embodiment, by comparing FIG. 3 and FIG. 4, the sequential order reveals compartments (such as compartments 104b and 104c) that are at a substantially similar position between the top of the housing and the bottom of the housing in a secondary sequential order from right to left. That is, the compartment 104b nearest a right side 130 of the housing 102 is revealed first (in FIG. 3) and then the compartment 104c that is to the left of compartment 104b is revealed (in FIG. 4). In other arrangements, such as the second arrangement of FIGS. 5 and 6, the sequential order may reveal compartments (such as compartments 104a, 104b, and 104c) that are at a substantially similar position between the top of the housing and the bottom of the housing in a secondary sequential order from left to right. That is, the compartment 104a nearest the left side 132 of the housing 102 is revealed first, followed by compartment 104b, and then compartment 104c. Other sequential orders of revealing the plurality of compartments 104 are also possible, such as a sequential order from either left-to-right or right-to-left, a sequential order that reveals compartments 104 located at substantially the same position between the right side 103 and the left side 132 in a sequential order from top-to-bottom or bottom-to-top, or a random order determined by the position of the compartments 104 as dictated by a design that minimizes or optimizes the size of the housing 102.

The second arrangement (FIGS. 5 and 6) and the third arrangement (FIGS. 7 and 8) both have a housing 102 including a paperboard box 134 and a tray 136 formed from die cut paperboard. The paperboard tray 136 is positioned within the paperboard box 134. A protective cover 138 is rotatably secured to the paperboard box 134. The paperboard tray 136 includes at least one channel 140 positioned adjacent at least one compartment (104a, 104b, 104c . . . ) of the plurality of compartments 104 to facilitate picking up at least one component (106a, 106b, 106c . . . ) of the plurality of components 106.

For example, the second arrangement (as shown in FIG. 5) includes a first channel 140a and a second channel 140b in the paperboard tray 134. Three compartments 104a, 104b, and 104c are connected by the first channel 140a, and a single compartment 104d is provided adjacent the second channel 140b. The compartment 104d adjacent the second channel 140b includes finger slots 142 to facilitate picking up the component 106d. In the second arrangement (as shown in FIG. 6), the protective cover 138 is connected to the paperboard box 134 at a hinge 144 along the left side 132 of the paperboard box 134 and the instruction manual 108 is connected to the paperboard box 134 along the hinge 144.

As another example, the third arrangement (as shown in FIG. 7) includes a channel 140 connected three compartments 104a, 104b, and 104c. In the third arrangement (as shown in FIG. 8), the instruction manual 108 is connected to a top surface 146 of the paperboard tray 136.

The fourth arrangement (FIGS. 9 and 10) and the fifth arrangement (FIGS. 11 and 12) both have a housing 102 that includes a paperboard box 134 and a tray 148 formed from recycled polyethylene tetraphyte (RPET). The rPET tray 148 is positioned within the paperboard box 134. A protective cover 138 is rotatably secured to the paperboard box 134. A compartment (104a, 104b, 104c . . . ) of the plurality of compartments 104 includes a form fitting recess 105 within the rPET tray 148. In the fourth and fifth arrangements (as shown in FIGS. 9 and 11), the rPET tray 148 includes four compartments 104a, 104b, 104c, and 104d including form fitting recesses 105. Two of the compartments 104b and 104d have finger slots 142 to facilitate picking up the components 106b and 106d.

In the fifth arrangement (as shown in FIG. 11), the housing 102 further includes a paperboard panel 152 with tuck flaps 154 configured to be secured over the rPET tray 148. Furthermore, in the fifth arrangement (as shown in FIG. 12), the instruction manual 108 is connected to the rPET tray 148 by binding tabs 156. The protective cover 138 is also secured to the rPET tray 148 by the binding tabs 156.

Color Coordination Drug Delivery Packaging

Figure 22:
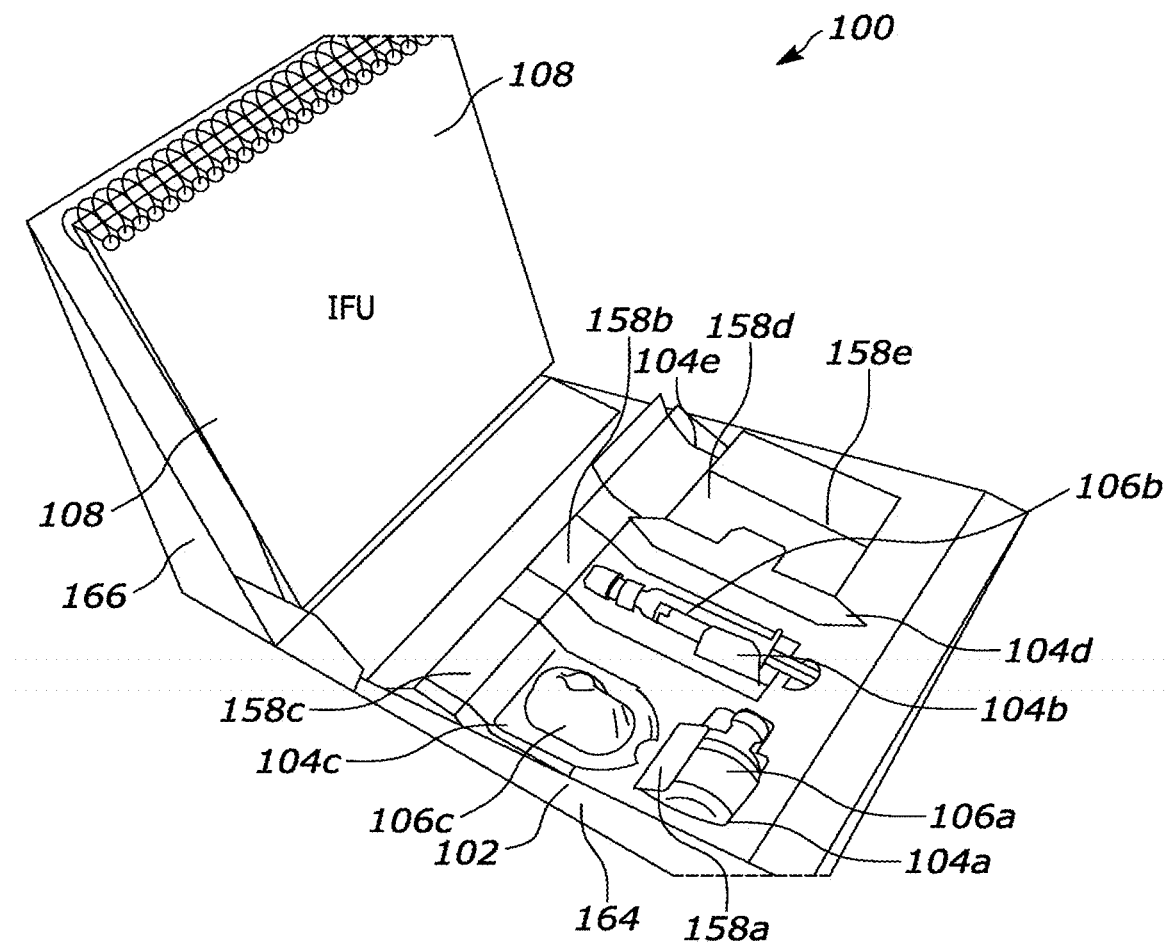
FIG. 22 is a perspective view of an eighth arrangement illustrating color coordination drug delivery packaging configured to elevate an instruction manual.
Figure 23:
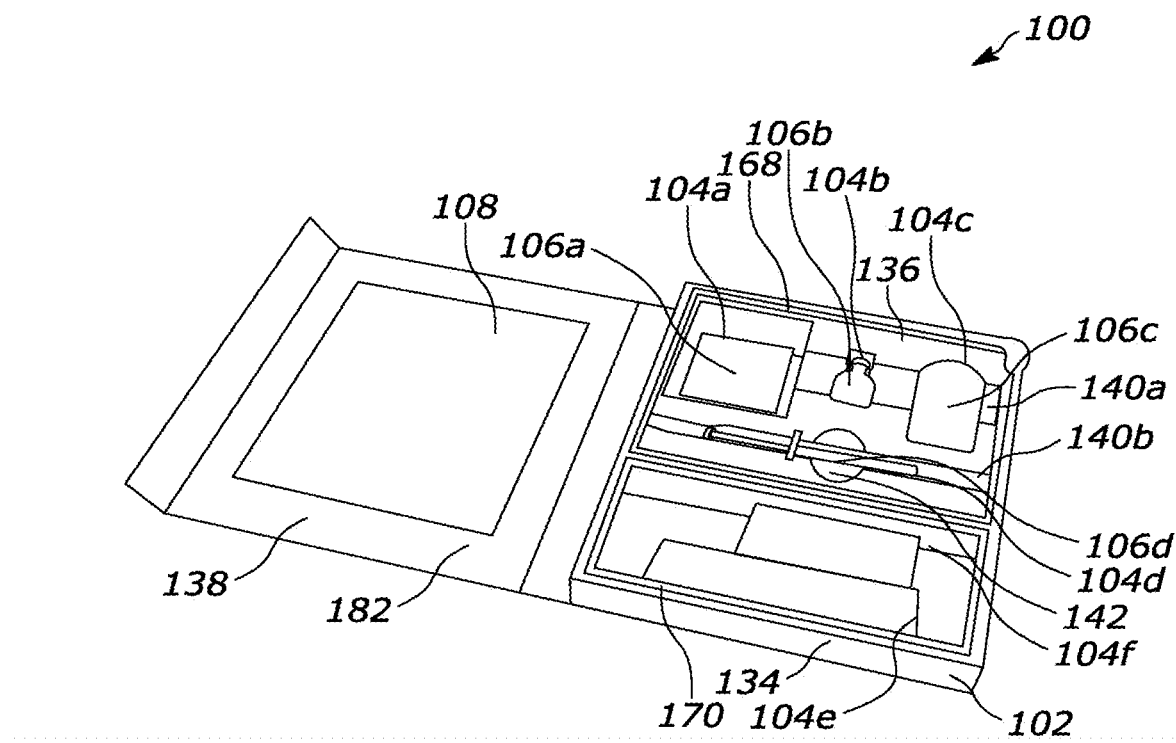
FIG. 23 is a perspective view of a ninth arrangement illustrating color coordination drug delivery packaging having a top-down paperboard tray.
Figure 24:
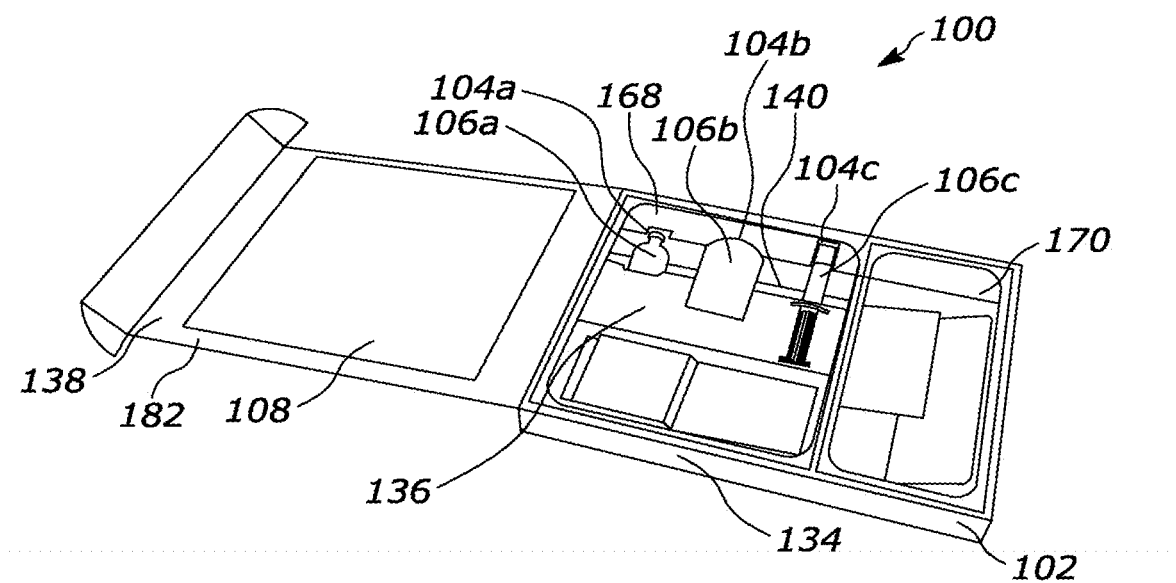
FIG. 24 is a perspective view of a tenth arrangement illustrating color coordination drug delivery packaging having a left-to-right paperboard tray.
Figure 25:
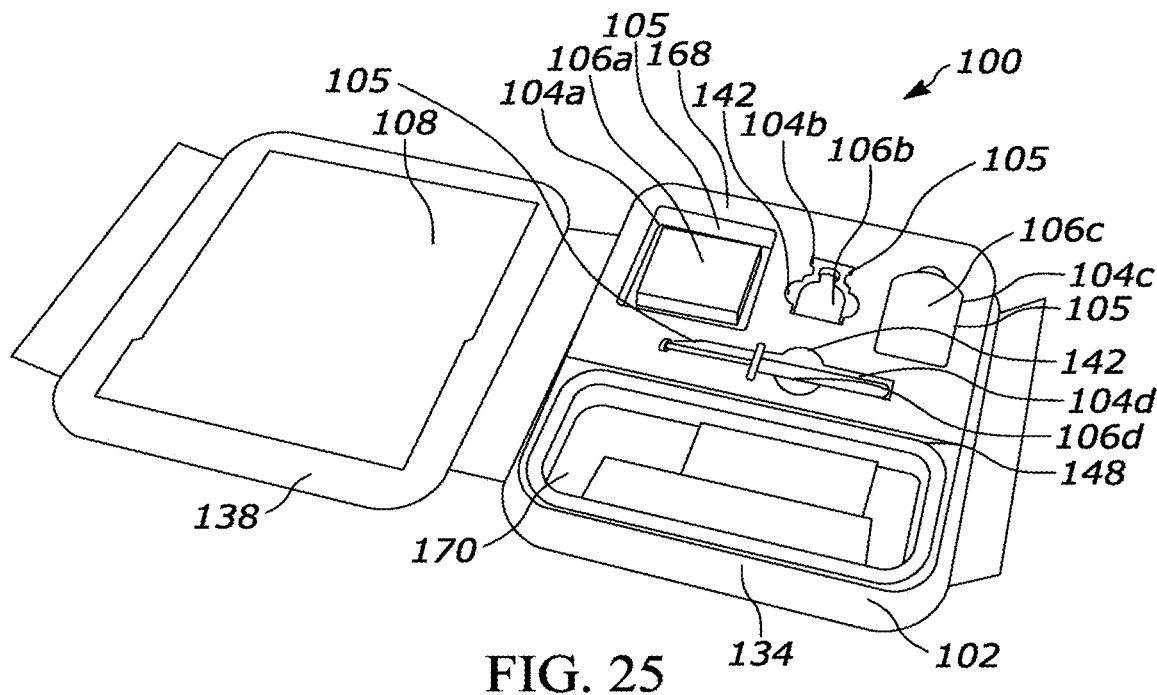
FIG. 25 is a perspective view of an eleventh arrangement illustrating color coordination drug delivery packaging having a top-down rPET tray.
Figure 26:
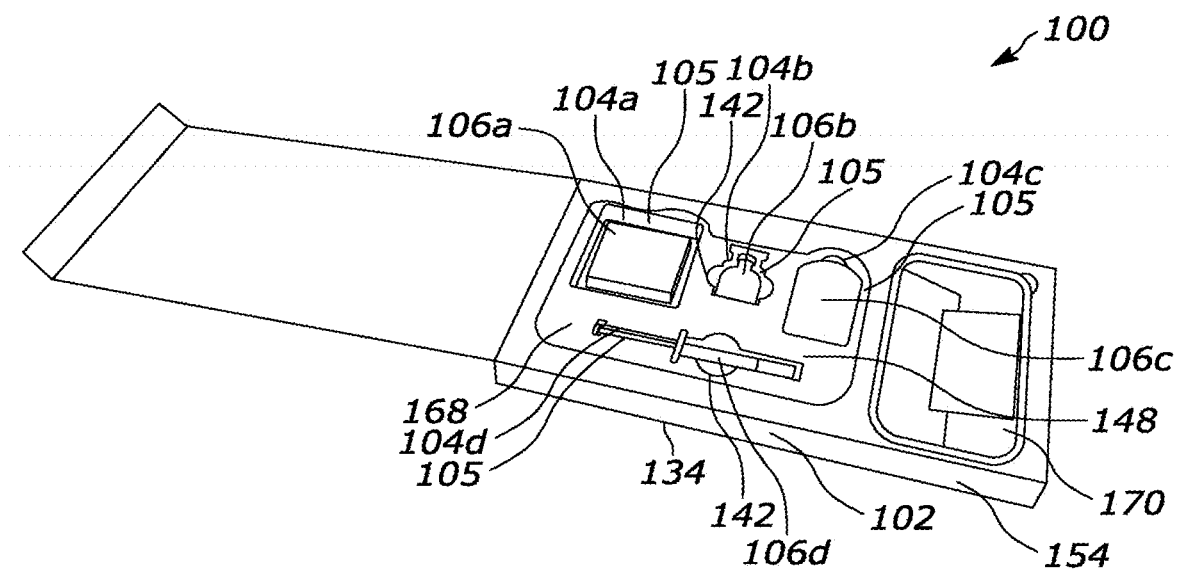
FIG. 26 is a perspective view of a twelfth arrangement illustrating color coordination drug delivery packaging having a left-to-right rPET tray.
Figure 27:
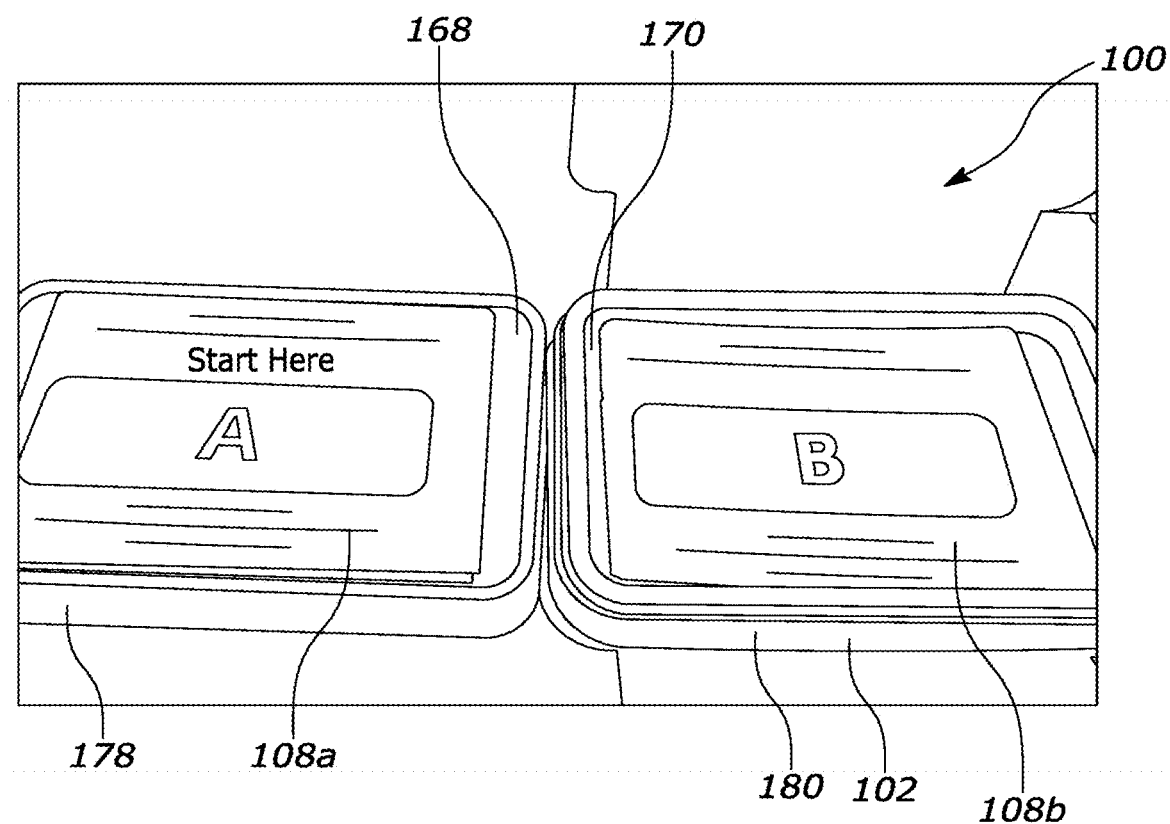
FIG. 27 is a perspective view of a thirteenth arrangement illustrating color coordination drug delivery packaging after disassembly.
Figure 28:
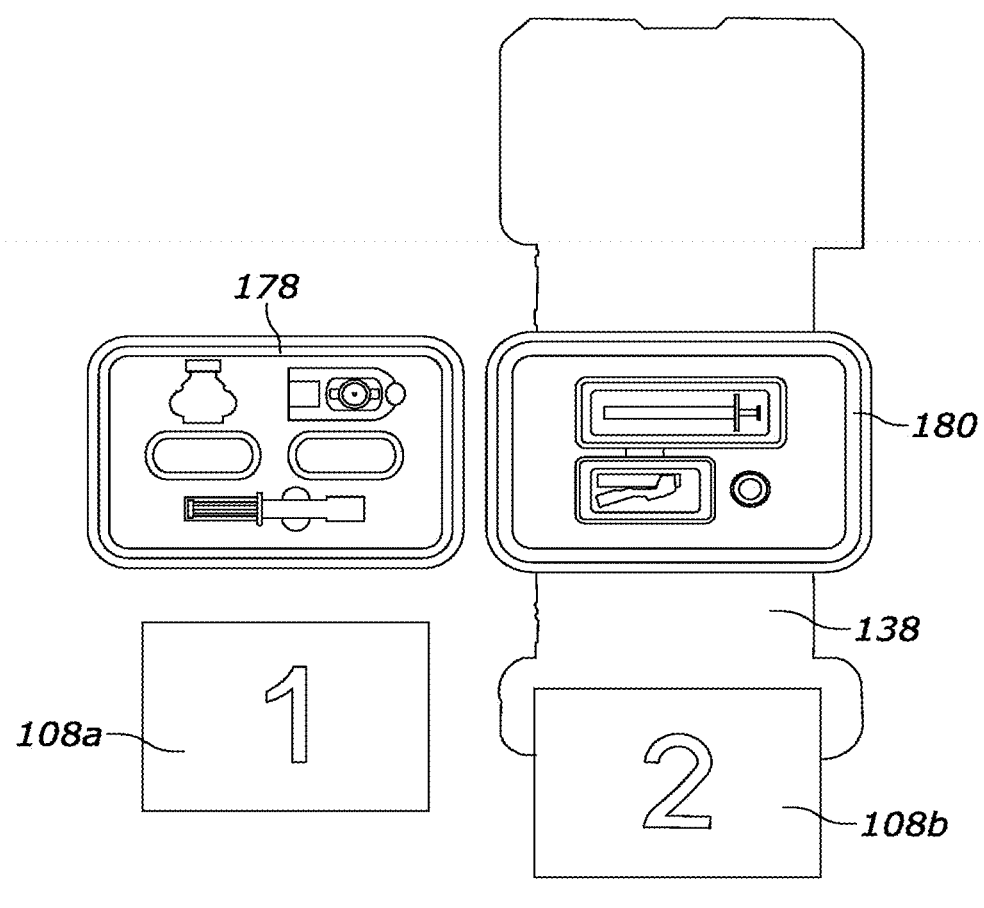
FIG. 28 is a top view of the thirteenth arrangement illustrating two trays having compartments.
Figure 29:
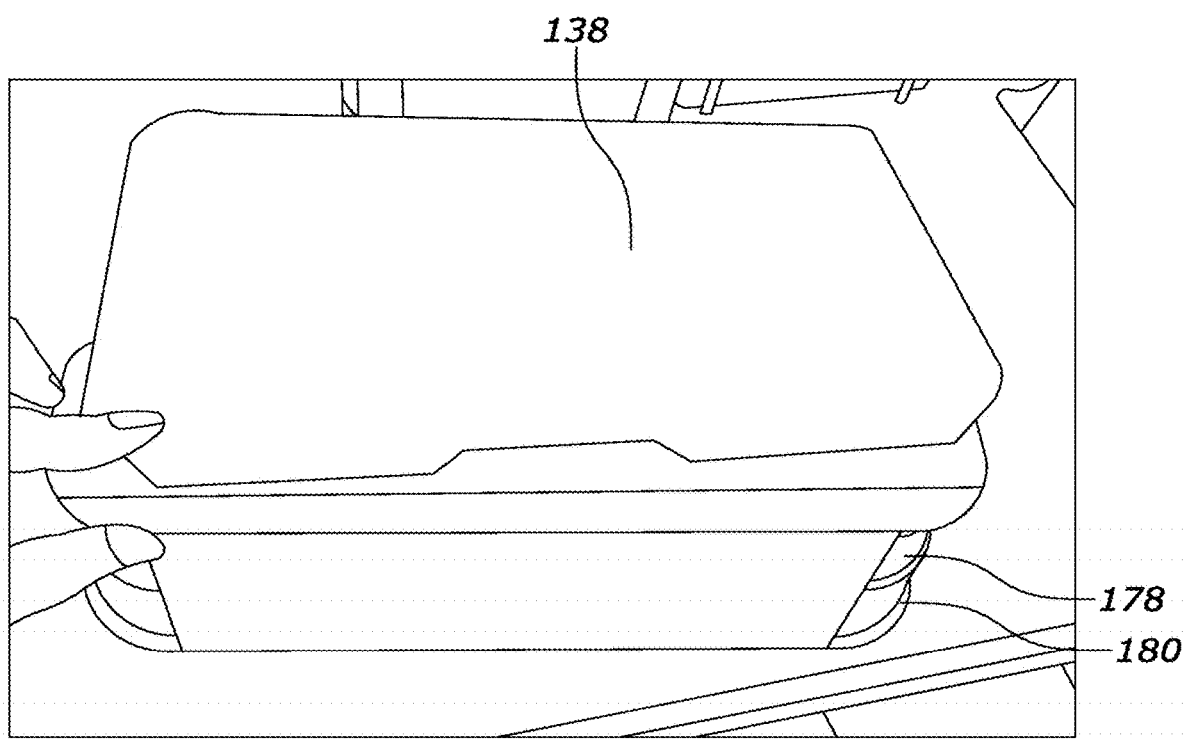
FIG. 29 is a perspective view of the thirteenth arrangement with the two tray assembled.

Eight arrangements of drug delivery device packaging kits 100 are disclosed in FIGS. 13-29, each illustrating the color coordination method discussed above. A sixth arrangement of drug delivery packaging is shown in FIGS. 13-17. A seventh arrangement of drug delivery packaging is shown in FIGS. 18-21. An eighth arrangement of drug delivery packaging is shown in FIG. 22. A ninth arrangement of drug delivery packaging is shown in FIG. 23. A tenth arrangement of drug delivery packaging is shown in FIG. 24. An eleventh arrangement of drug delivery packaging is shown in FIG. 25. A twelfth arrangement of drug delivery packaging is shown in FIG. 26. A thirteenth arrangement of drug delivery packaging is shown in FIGS. 27-29.

Common features in each of the sixth, seventh, eighth, ninth, tenth, eleventh, twelfth, and thirteenth arrangements are identified by the same reference number. Moreover, some of the features in the first through fifth arrangements discussed above are also present in one or more of the sixth through thirteenth arrangements and are identified by the same reference number. After their initial introduction, common features are not described in substantial detail. Unique features are identified by unique reference numbers. Any combination or sub-combination of features described in regard to the sixth, seventh, eighth, ninth, tenth, eleventh, twelfth, and thirteenth arrangements may be incorporated into another of the sixth, seventh, eighth, ninth, tenth, eleventh, twelfth, and thirteenth arrangements, and vice-versa. Likewise, any combination or sub-combination of features described in regard to the first through fifth arrangements may be incorporated into one of the sixth through thirteenth arrangements, and vice versa. While the progressive display and color coordination methods are explained using different arrangements, both methods may be incorporated into a single arrangement. For example, the first arrangement of FIGS. 1-4 could include the color coordination features described with respect to the sixth arrangement of FIGS. 13-17 to provide guidance to a user in multiple ways.

While each of the drug delivery packaging kits 100 shown in the sixth, seventh, eighth, ninth, tenth, eleventh, twelfth, and thirteenth arrangements are directed to packaging for a single drug delivery device, the drug delivery packaging kits 100 could also be used for a drug delivery system including multiple drug delivery devices. A drug delivery packaging kit 100 for a drug delivery system would operate according to the same principles described below but assembly of the components contained within the drug delivery packaging kit 100 according to the instructions provided therein would result in the assembly of multiple drug delivery devices instead of just one drug delivery device.

In the sixth through thirteenth arrangements (FIGS. 13-29), a kit 100 for a drug delivery device includes a color 158 displayed with a respective compartment (104a, 104b, 104c . . . ) of the plurality of compartments 104. The color 158 is also displayed with a respective component step (120a, 120b, 120c . . . ) associated with the respective compartment (104a, 104b, 104c . . . ) and with at least one of the plurality of components 106 to be secured within the respective compartment (104a, 104b, 104c . . . ). The color 158 is configured to direct a user reading the respective component step (120a, 120b, 120c . . . ) to the associated at least one of the plurality of components 106.

Figure 13:
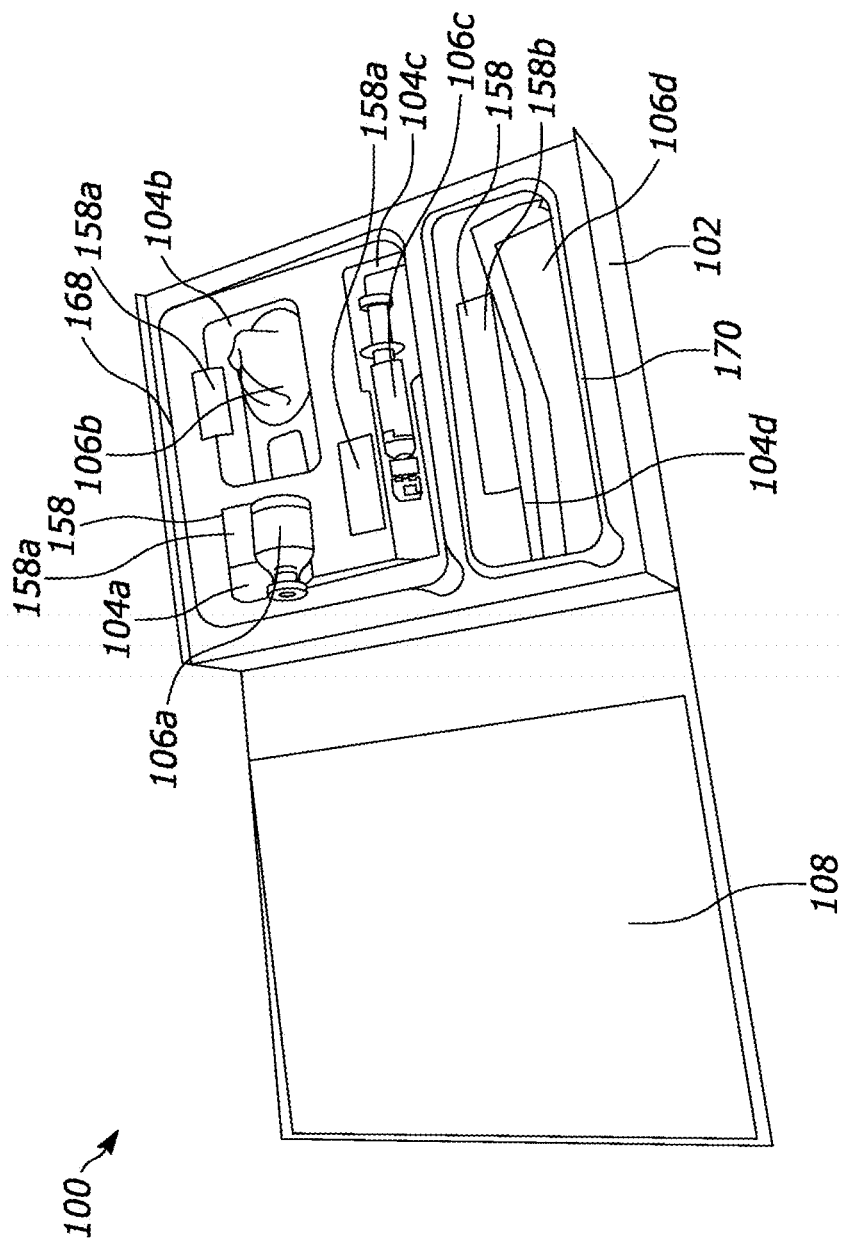
FIG. 13 is a perspective view of a sixth arrangement illustrating color coordination drug delivery packaging.

For example, in FIG. 13, a bright blue color 158 is displayed with compartment 104a. The bright blue color 158 is also displayed with a respective component step 120a shown in FIG. 15. The component step 120a is associated with the component 106a (i.e., the product vial) because it describes a first use of the product vial and is further associated with the compartment 104a in which the component 106a (i.e., the product vial) is configured to be secured because that is where the user will need to look to find the component 106a (i.e., the product vial).

Figure 14:
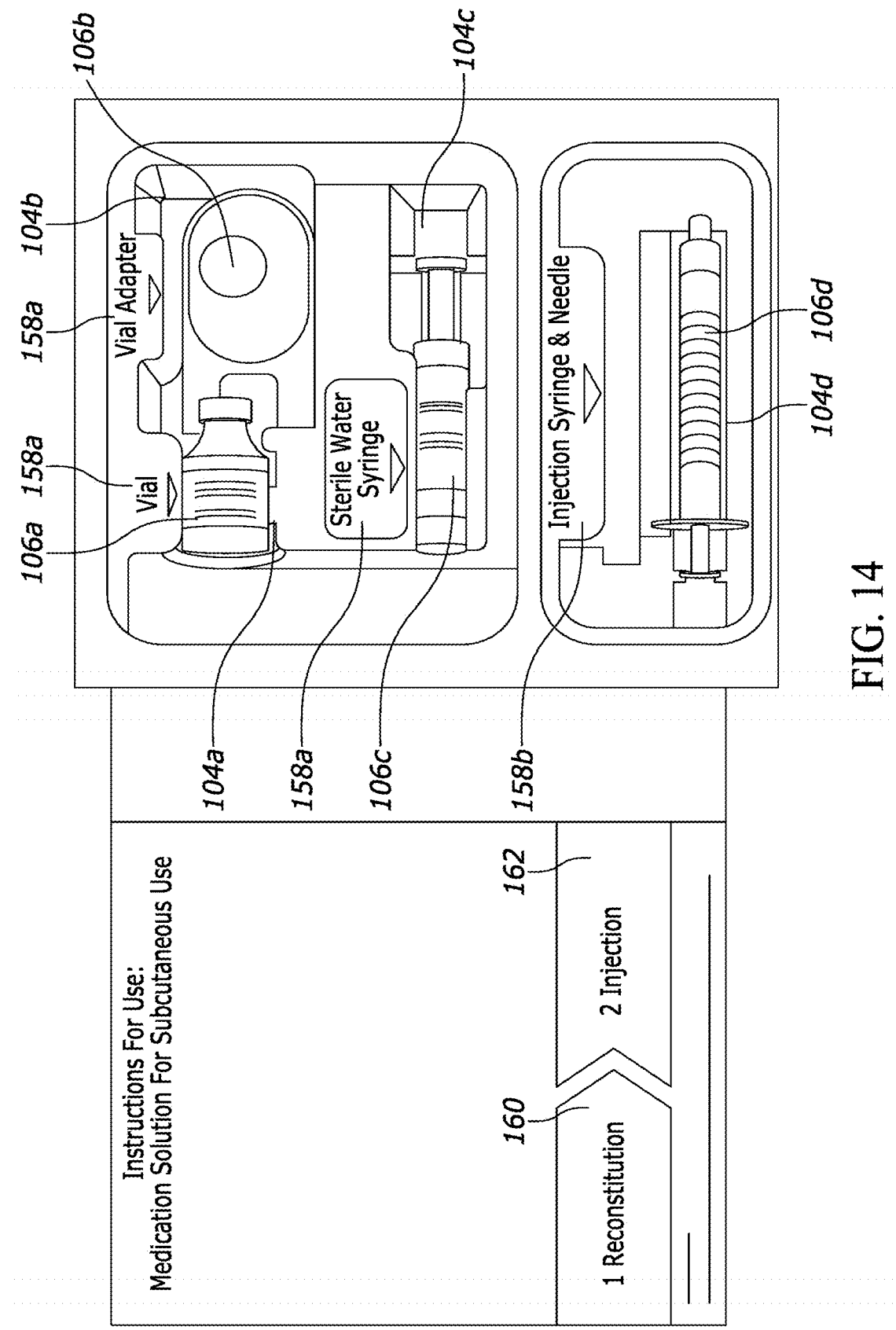
FIG. 14 is a top view of the sixth arrangement of FIG. 13 illustrating the color coordination between compartments of a housing and an instruction manual.
Figure 15:
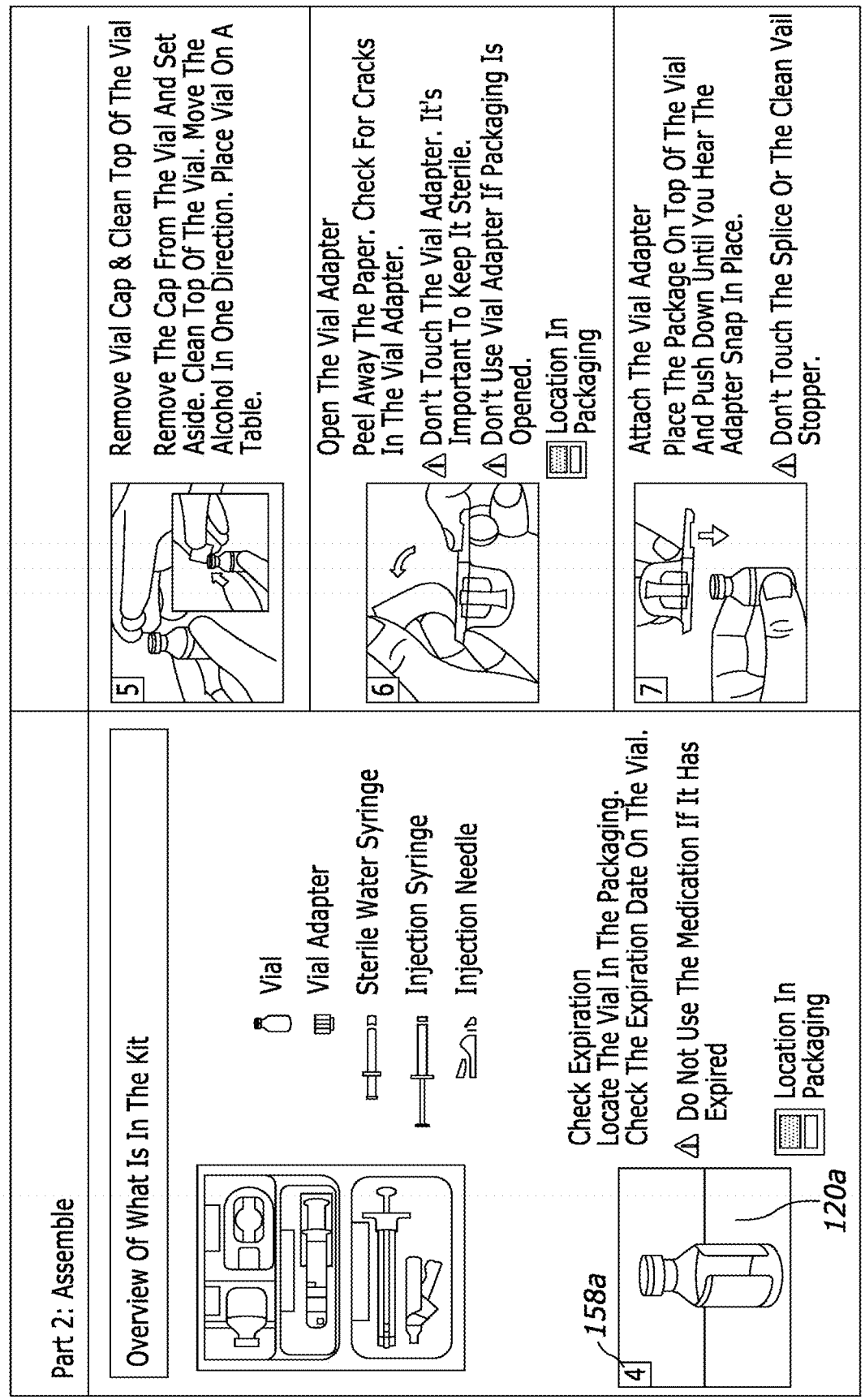
FIG. 15 is a top view of an instruction manual of the sixth arrangement of FIGS. 13 and 14 illustrating a first color used for color coordination.
Figure 16:
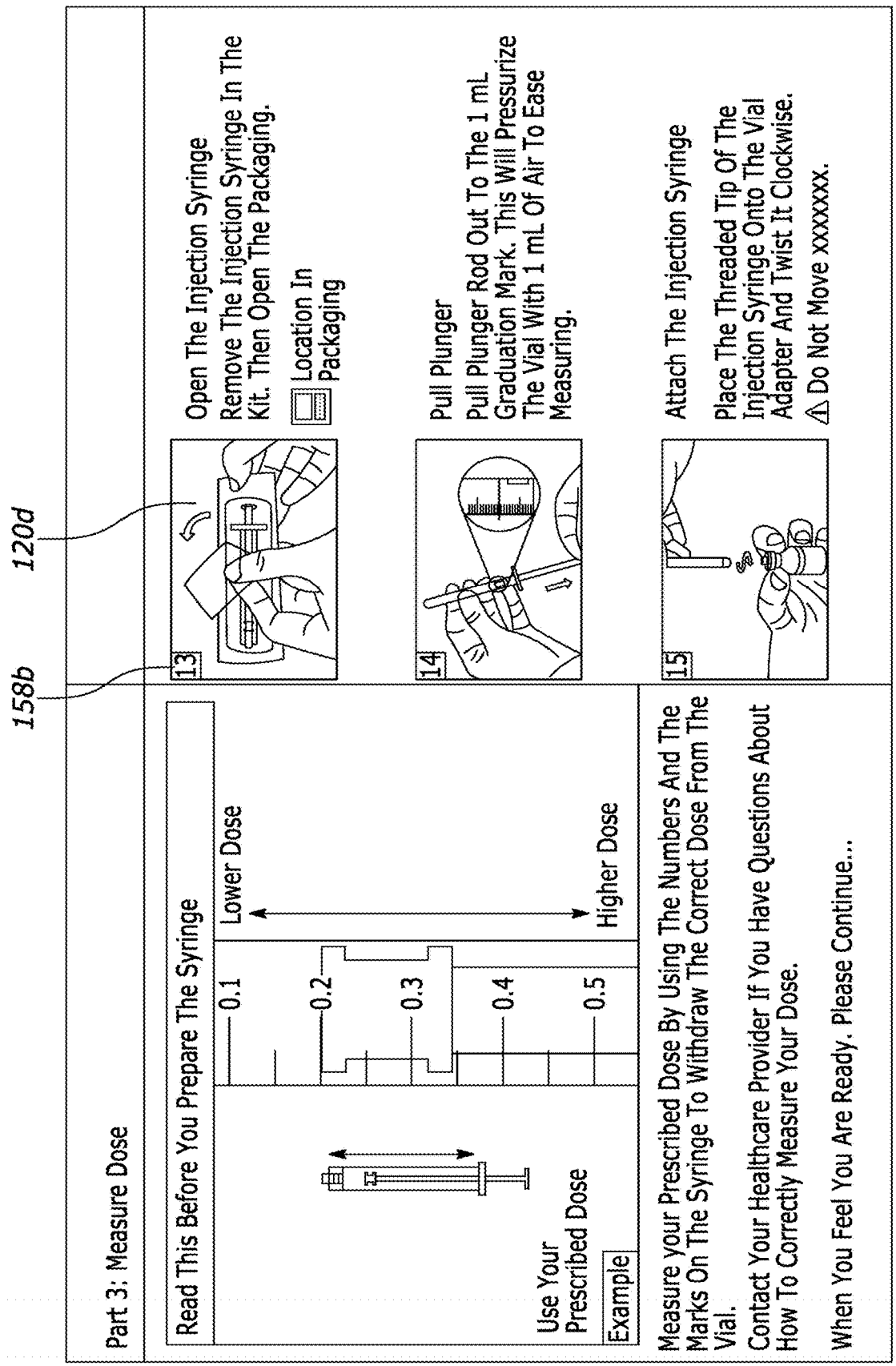
FIG. 16 is a top view of the instruction manual of the sixth arrangement of FIGS. 13-15 illustrating a second color used for color coordination.
Figure 17:
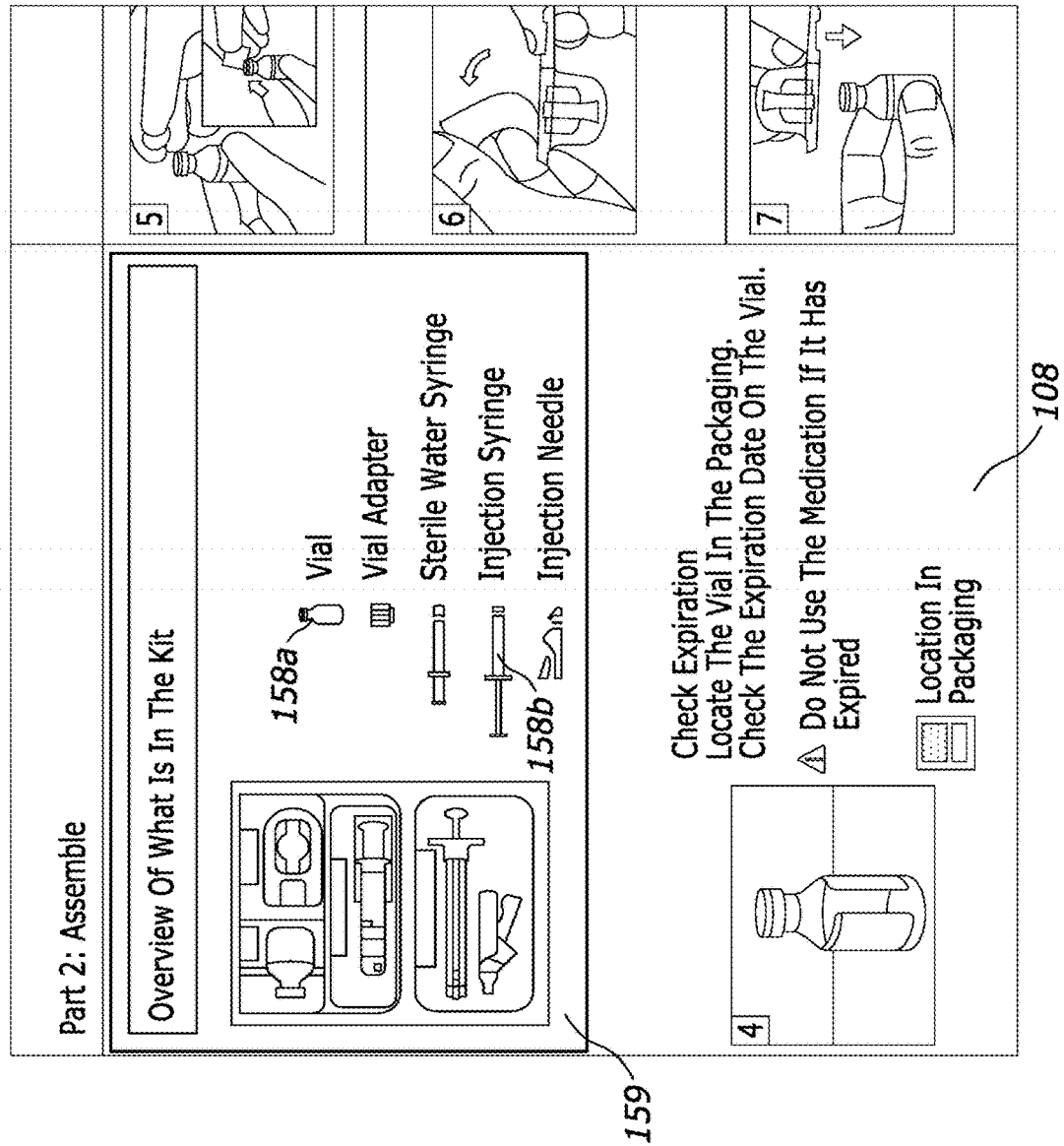
FIG. 17 is a top view of a color coordination graphic contained within the instruction manual of the sixth arrangement of FIGS. 13-16.

In the sixth arrangement (FIGS. 13-17) and the seventh arrangement (FIGS. 18-21), the series of steps 118 include a first subset of steps 160 and a second subset of steps 162. For example, as shown in FIG. 14, the instruction manual 108 includes a first subset 160 directed to reconstitution of the drug and a second subset 162 directed to injection of the drug. Each component step (120a, 120b, 120c, . . . ) is assigned to either the first subset or the second subset. For example, a component step (e.g., 120*a*, 120*b*, 120*c*, . . . ) necessary for reconstituting the drug would be assigned to the first subset 160, and a component step (e.g., 120*d* . . . ) necessary for injecting the drug would be assigned to the second subset 162. The color 158 is a first color 158*a* displayed with component steps assigned to the first subset (e.g., 120*a*, 120*b*, 120*c*) and compartments associated with the component steps assigned to the first subset (e.g., 104*a*, 104*b*, 104*c*). Specifically, color 158*a* in the sixth and seventh arrangements is bright blue. A second color 158*b* is displayed with component steps assigned to the second subset (e.g., 120*d*) and compartments associated with the component steps assigned to the second subset (e.g., 106*d*). Specifically, the color 158*b* in the sixth and seventh arrangements is dark turquoise. As shown in FIG. 17, the sixth arrangement also includes a legend 159 further clarifying use of the colors 158*a* and 158*b*. Bright blue and dark turquoise for colors 158*a* and 158*b* are merely examples and any other colors could be used instead.

In the eighth arrangement (FIG. 22), a unique color 158 (158*a*, 158*b*, 158*c* . . . ) is displayed with each component step (120*a*, 120*b*, 120*c* . . . ) and the compartment (104*a*, 104*b*, 104*c* . . . ) associated therewith. For example, color 158*a* is dark blue, color 158*b* is light blue, color 158*c* is yellow, color 158*d* is green, and color 158*e* is pink. Other colors could be used instead. The housing 102 includes a base 164 comprising the plurality of compartments 104 and a cover 166 connected to the base at a hinge 144. The instruction manual 108 is connected to the cover 166. The cover 166 is configured to cover the plurality of compartments 104 is a first orientation, and the cover 166 is configured to hold the instruction manual 108 upright in a second orientation. Beneficially, when the cover 166 is in the second orientation, the instruction manual 108 easily visible to a user and is optimally located near the plurality of compartments 104 to facilitate finding a component (e.g., 106*a*, 106*b*, 106*c*) identified in the instruction manual 108.

Multiple Chamber Drug Delivery Packaging

Several of the arrangements discussed above also illustrate the multiple chamber method discussed above. Specifically, the second arrangement (FIGS. 5-6), the third arrangement (FIGS. 7-8), the fourth arrangement (FIGS. 9-10), the sixth arrangement (FIGS. 13-17), the seventh arrangement (FIGS. 18-21), the ninth arrangement (FIG. 23), the tenth arrangement (FIG. 24), the eleventh arrangement (FIG. 25), the twelfth arrangement (FIG. 26), and the thirteenth arrangement (FIGS. 27-29) illustrate the multiple chamber method.

Common features in each of the second, third, fourth, sixth, seventh, ninth, tenth, eleventh, twelfth, and thirteenth arrangements are identified by the same reference number. After their initial introduction, common features are not described in substantial detail. Unique features are identified by unique reference numbers. Any combination or sub-combination of features described in regard to the second, third, fourth, sixth, seventh, ninth, tenth, eleventh, twelfth, and thirteenth arrangements may be incorporated into another of the second, third, fourth, sixth, seventh, ninth, tenth, eleventh, twelfth, and thirteenth arrangements, and vice-versa. Likewise, any combination or sub-combination of features described in regard to the second, third, fourth, sixth, seventh, ninth, tenth, eleventh, twelfth, and thirteenth arrangements may be incorporated into one of the first, fifth, and eighth arrangements, and vice versa. While the multiple chamber method is explained using only a subset of the arrangements disclosed herein, the multiple chamber method could be incorporated into other arrangements including arrangements using the progressive display method, the color coordination method, or both the progressive display and color coordination methods. For example, the first arrangement of FIGS. 1-4 could include the color coordination features described with respect to the sixth arrangement of FIGS. 13-17 and could also include the multiple chambers described with respect the second arrangement of FIGS. 5-6 to provide guidance to a user in at least three ways.

While each of the drug delivery packaging kits 100 shown in the second, third, fourth, sixth, seventh, ninth, tenth, eleventh, twelfth, and thirteenth arrangements are directed to packaging for a single drug delivery device, the drug delivery packaging kits 100 could also be used for a drug delivery system including multiple drug delivery devices. A drug delivery packaging kit 100 for a drug delivery system would operate according to the same principles described below but assembly of the components contained within the drug delivery packaging kit 100 according to the instructions provided therein would result in the assembly of multiple drug delivery devices instead of just one drug delivery device.

In the second, third, fourth, sixth, seventh, ninth, tenth, eleventh, twelfth, and thirteenth arrangements, each compartment (104*a*, 104*b*, 104*c* . . . ) is positioned within a first chamber 168 or a second chamber 170. As described above, the series of steps 118 includes a first subset 160 and second subset 162 that may, for example, relate to the reconstitution of the drug and the injection of the drug. Each component step (120*a*, 120*b*, 120*c* . . . ) is assigned to either the first subset 160 or the second subset 162. The first chamber 168 includes each respective compartment (e.g., in FIGS. 23, 104*a*, 104*b*, 104*c*, 104*d*) associated with each component step (e.g., 120*a*, 120*b*, 120*c*, 120*d*) assigned to the first subset of steps 160. The second chamber 170 includes each respective compartment (e.g., in FIG. 23, 104*e*, 104*f*) associated with each component step (e.g., 120*e*, 120*f*) assigned to the second subset of steps 170. A user using a two compartment arrangement is able to eliminate all compartments 104 not relevant to the subset of steps (e.g., 160, 162) they are currently performing from consideration, thereby reducing the number of compartments 104 and components 106 that must be reviewed for any given component step (120*a*, 120*b*, 120*c* . . . ).

In some arrangements, such as the ninth arrangement shown in FIG. 23, the first chamber 168 and the second chamber 170 are sealed separately from one another. Beneficially, this helps to secure the components 106 during shipping and handling to protect the components 106 from damage. In some arrangements, such as that shown in FIG. 13, all compartments (e.g., 104*a*, 104*b*, 104*c*) within the first chamber 168 are displayed with a first color 158*a*, and all compartments (e.g., 104*d*) in a second chamber 170 are displayed with a second color 158*a*, the first color 158*a* also being displayed with all of the first subset of steps 160 and the second color also being displayed with all of the second subset of steps 162. This is one exemplary way in which the multiple chamber method and the color coordination methods can be combined.

Figure 18:
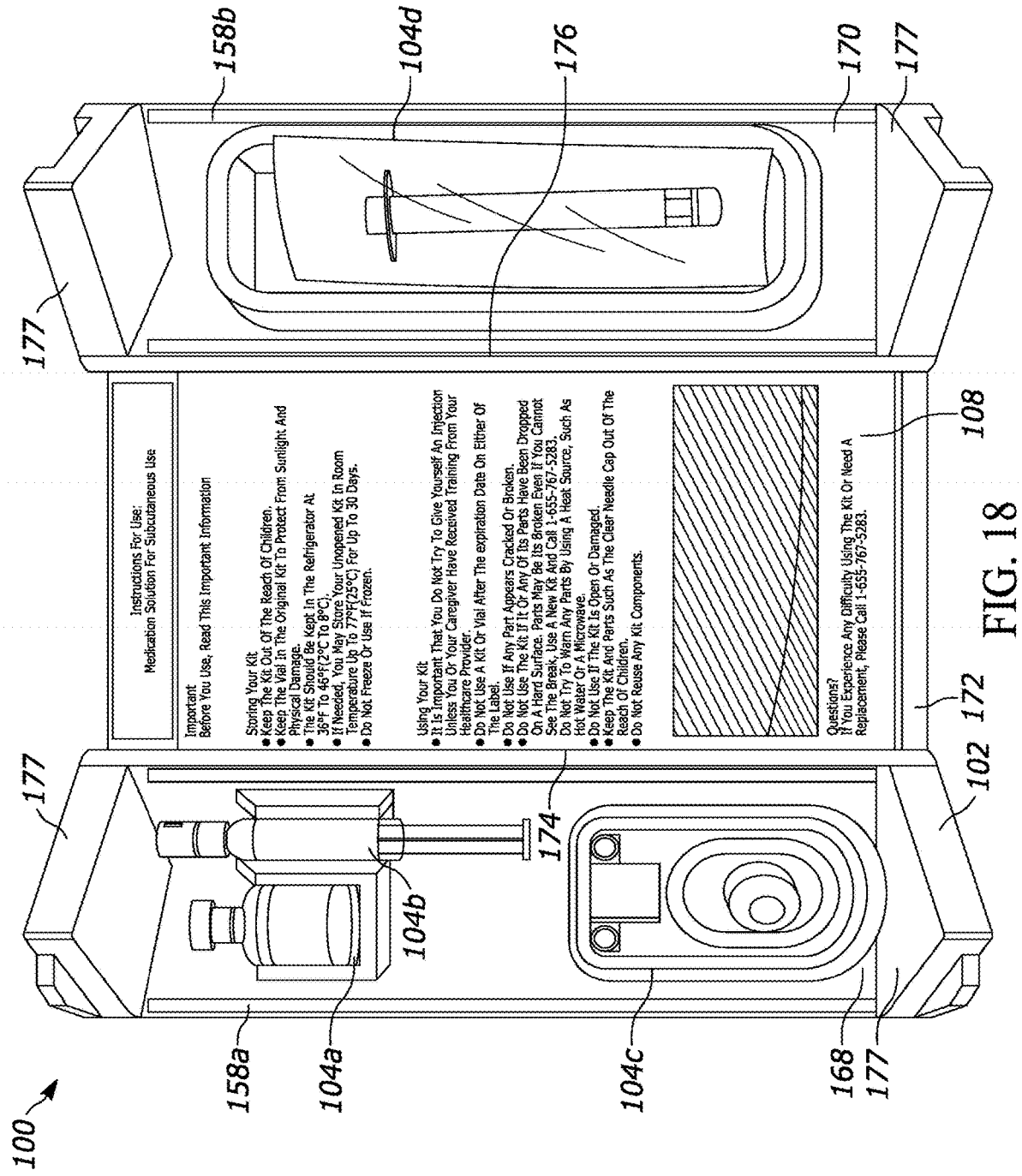
FIG. 18 is a top view of a seventh arrangement illustrating color coordination drug delivery packaging having a roll-out structure in an open configuration.
Figure 19:
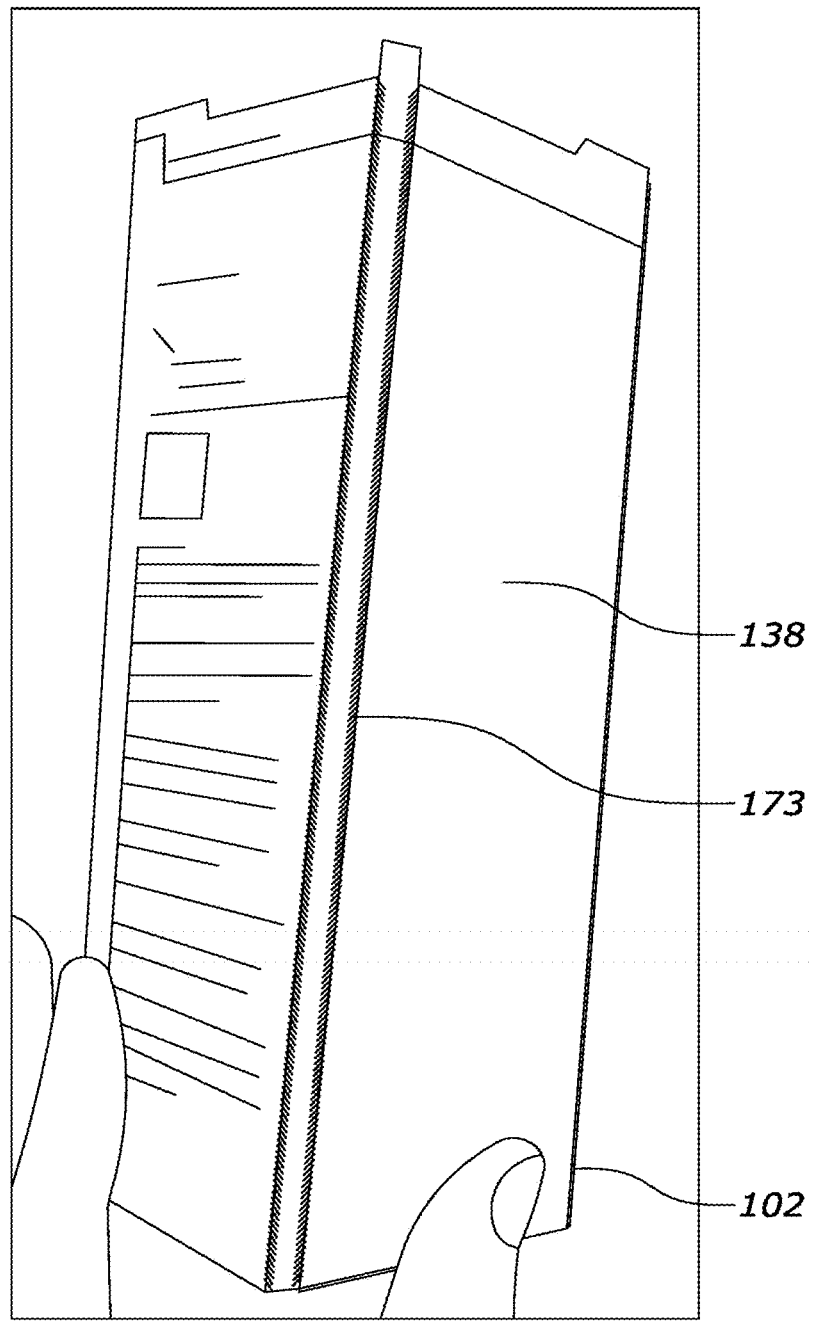
FIG. 19 is a perspective view of the seventh arrangement of FIG. 18 in a closed configuration.
Figure 20:
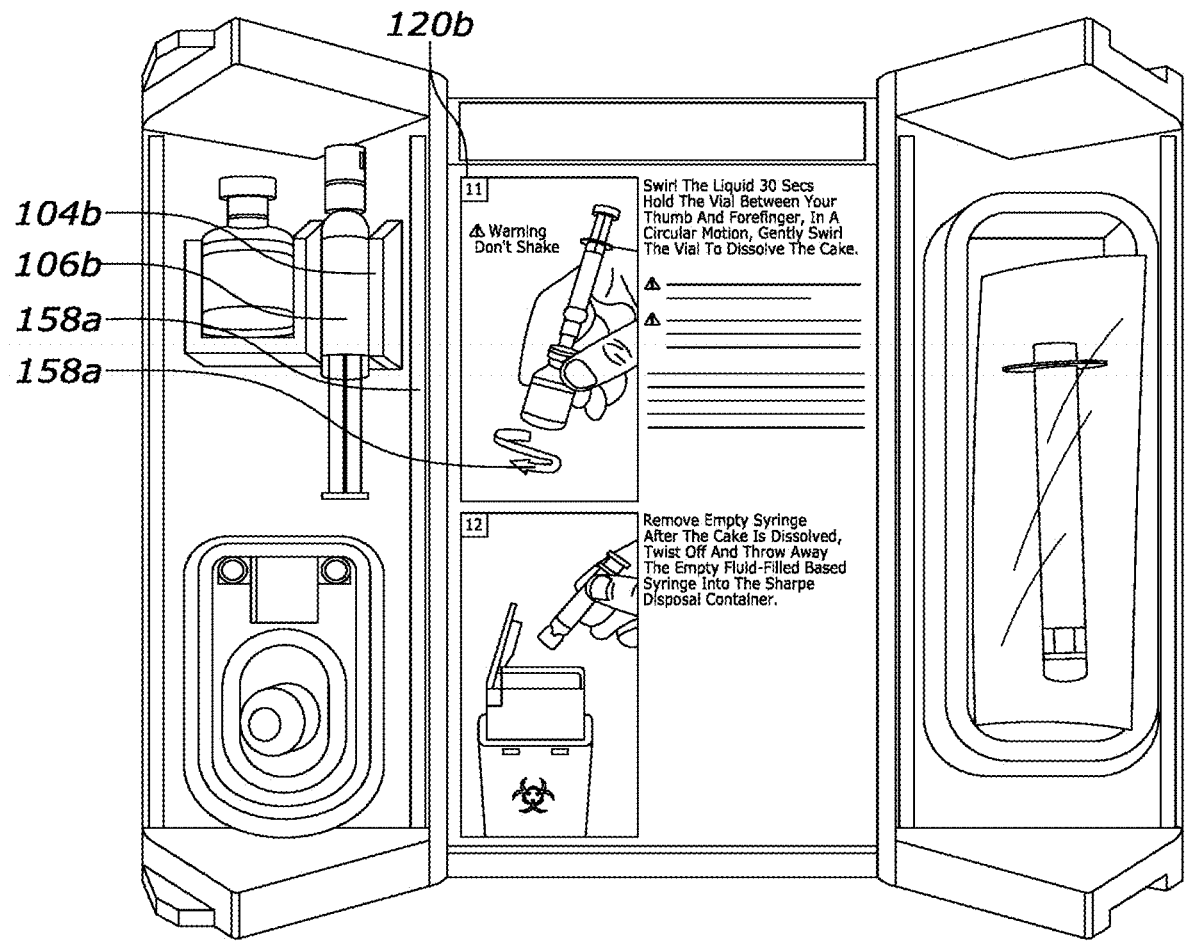
FIG. 20 is a top view of the seventh arrangement of FIGS. 18 and 19 illustrating a first color used for color coordination.
Figure 21:
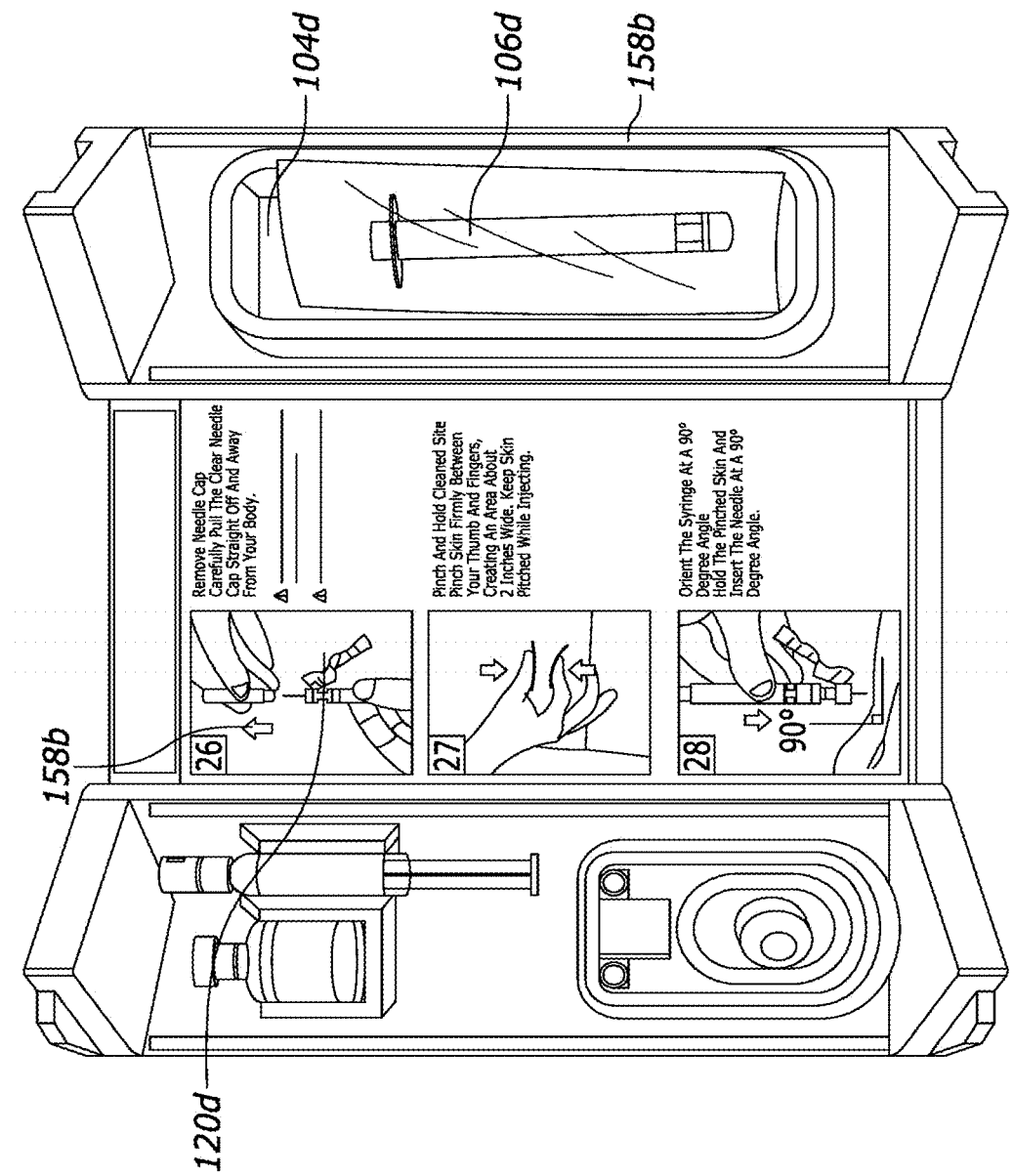
FIG. 21 is a top view of the seventh arrangement of FIGS. 18-20 illustrating a second color used for color coordination.

In the seventh arrangement (FIGS. 18-21), the housing 102 has a central instruction surface 172 on which the instruction manual 108 is disposed. The first chamber 168 is hingedly connected to the central instruction surface 172 on a first side 174, and the second chamber 170 is hingedly connected to the central instruction surface 172 on a second side 176. The housing 102 is configured to transition between an open configuration where the plurality of compartments 104 (104a, 104b, 104c, 104d) are accessible for use (as shown in FIG. 18) and a closed configuration where the first chamber 168 and the second chamber 170 are each rotated relative to the central instruction surface 172 and connected to one another to prevent access to the plurality of compartments 104. In the closed configuration, as shown in FIG. 19, the protective cover 138 may be wrapped around the housing 102 and may include a tear strip 173 to facilitate an initial opening of the protective cover 138. In the seventh arrangement, as shown in FIG. 18, the first chamber 168 and the second chamber 172 each include two end structures 177, and the connection between the first chamber 168 and the second chamber 170 in the closed configuration is achieved by connecting the end structures 177.

In the thirteenth arrangement (FIGS. 27-29), the housing 102 includes a first tray 178 including the first chamber 168 and a second tray 180 including the second chamber 170. The first tray 178 is configured to be stackable on the second tray 180. The instruction manual 108 may be divided into two parts, a first part 180a including the first subset 160 of steps (e.g., steps relating to the reconstitution of the drug) and a second part 180b including the second subset 162 (e.g., steps relating to injection of the drug). The first part 108a may be provided with the first tray 178, and the second part 108b may be provided with the second tray 180. The protective cover 138 may be configured to wrap around both the first tray 178 and the second tray 180 in order to assist with securing the first tray 178 and the second tray 180 together. Optionally, the first tray 178 and the second tray 180 may be made from paperboard.

The ninth arrangement (FIG. 23) and the tenth arrangement (FIG. 24) both have a housing 102 including a paperboard box 134 and a tray 136 formed from die cut paperboard. The paperboard tray 136 is positioned within the paperboard box 134 and includes the first chamber 168 and the second chamber 170. A protective cover 138 is rotatably secured to the paperboard box 134. The first chamber 168 includes at least one channel 140 positioned adjacent at least one compartment (104a, 104b, 104c . . . ) of the plurality of compartments 104 to facilitate picking up at least one component (106a, 106b, 106c . . . ) of the plurality of components 106.

For example, the ninth arrangement (as shown in FIG. 23) includes a first channel 140a and a second channel 140b in the first chamber 168. Three compartments 104a, 104b, and 104c are connected by the first channel 140a, and a single compartment 104d is provided adjacent the second channel 140b. The compartment 104d adjacent the second channel 140b includes finger slots 142 to facilitate picking up the component 106d. The second chamber 170 is positioned below the first chamber 168. In the ninth arrangement, the instruction manual 108 is connected to a back surface 182 of the protective cover 138.

As another example, the tenth arrangement (as shown in FIG. 24) includes a channel 140 connected three compartments 140a, 140b, and 140c in the first chamber 168. The second chamber 170 is positioned to the right of the first chamber 168. For purposes of this specification, left and right are determined from the perspective of a user looking at the plurality of compartments 104. The instruction manual 108 is connected to a back surface 182 of the protective cover 138.

The eleventh arrangement (FIG. 25) and the twelfth arrangement (FIG. 26) both have a housing 102 that includes a paperboard box 134 and a tray 148 formed from recycled polyethylene tetraphyte (RPET). The rPET tray 148 is disposed within the paperboard box 134. A protective cover 138 is rotatably secured to the paperboard box 134. The rPET tray 148 includes the first chamber 168 and the second chamber 170. Each compartment (104a, 104b, 104c . . . ) of the plurality of compartments 104 positioned within the first chamber 168 is defined by a form fitting recess 105 within the rPET tray 148. In the eleventh and twelfth arrangements (as shown in FIGS. 25 and 26), the rPET tray 148 includes four compartments 104a, 104b, 104c, and 104d including form fitting recesses 105 in the first chamber 168. Two of the compartments 104b and 104d have finger slots 142 to facilitate picking up the components 106b and 106d. In the eleventh arrangement (shown in FIG. 25), the second chamber 170 is below the first chamber 168. In the twelfth arrangement (shown in FIG. 26), the second chamber 170 is to the right of the first chamber 168 and a paperboard panel 152 with tuck flaps 154 is secured over the rPET tray 148.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings. Additionally, the described embodiments/examples/implementations should not be interpreted as mutually exclusive, and should instead be understood as potentially combinable if such combinations are permissive in any way. In other words, any feature disclosed in any of the aforementioned embodiments/examples/implementations may be included in any of the other aforementioned embodiments/examples/implementations.

The benefits, advantages, solutions to problems, and any element(s) that may cause any benefit, advantage, or solution to occur or become more pronounced are not to be construed as a critical, required, or essential features or elements of any or all the claims. The claimed invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The patent claims at the end of this patent application are not intended to be construed under 35 U.S.C. § 112 (f) unless traditional means-plus-function language is expressly recited, such as "means for" or "step for" language being explicitly recited in the claim(s).

What is claimed is:

1. A kit for a drug delivery device or system comprising:
   a housing having a plurality of compartments;
   a plurality of components of the drug delivery device or system, each component of the plurality of components configured to be secured within a compartment of the plurality of compartments of the housing;
   an instruction manual having a plurality of pages connected to the housing along a binding axis and arranged in a progressive order, each page of the plurality of pages configured to rotate from a first position on a first side of the binding axis to a second position on a second side of the binding axis;
   a series of steps for using and/or assembling the drug delivery device or system provided within the instruction manual, the series of steps including component steps, each component step associated with at least one of the plurality of components; and
   a plurality of component pages included within the plurality of pages, each component page displaying a respective component step, each component page associated with a compartment of the plurality of compartments that is configured to secure the at least one of the plurality of components associated with the respective component step, each component page sized and configured to not overlay the associated compartment in the first position;
   all pages of the plurality of pages preceding a respective component page of the plurality of component pages in the progressive order sized and configured to overlay the associated compartment of the respective component page in the first position such that the respective component page and the associated compartment are first displayed together to a user using the instruction manual in the progressive order.

2. The kit of claim 1, the binding axis positioned such that the first position of each page is to the right of the second position of each page.

3. The kit of claim 1, the plurality of compartments positioned such that a user using the instruction manual in the progressive order will reveal the plurality of compartments in a sequential order from a top of the housing to a bottom of the housing.

4. The kit of claim 3, wherein the sequential order reveals compartments of the plurality of compartments that are at a substantially similar position between the top of the housing and the bottom of the housing in a secondary sequential order from left to right.

5. The kit of claim 1, wherein the housing includes a box, a tray positioned within the box, and a protective cover rotatably secured to the box, the tray including at least one channel positioned adjacent at least one compartment of the plurality of compartments to facilitate picking up at least one component of the plurality of components.

6. The kit of claim 5, wherein the protective cover is connected to the box at a hinge and the instruction manual is connected to the box along the hinge.

7. The kit of claim 5, wherein the instruction manual is connected to a top surface of the tray.

8. The kit of claim 1, wherein the housing includes a box, a tray positioned within the box, and a protective cover rotatably secured to the box, wherein a compartment of the plurality of compartments includes a form fitting recess within the tray for one of the components of the plurality of components.

9. The kit of claim 5, the housing further comprising a panel with tuck flaps configured to be secured over the tray.

10. The kit of claim 5, wherein the instruction manual is connected to the tray by binding tabs.

11. A kit for a drug delivery device or system comprising:
    a housing having a plurality of compartments, each compartment positioned within a first chamber or a second chamber;
    a plurality of components of the drug delivery device or system, each component of the plurality of components configured to be secured within a compartment of the plurality of compartments of the housing; and
    an instruction manual having a plurality of pages, a series of steps for using and/or assembling the drug delivery device or system provided on the plurality of pages, the series of steps including
       a first subset of steps,
       a second subset of steps, and
       component steps, each component step assigned to either the first subset or the second subset, each component step associated with a respective at least one of the plurality of components and with a respective compartment of the plurality of compartments configured to secure the respective at least one of the plurality of components;
    the first chamber including each respective compartment associated with each component step assigned to the first subset of steps;
    the second chamber including each respective compartment associated with each component step assigned to the second subset of steps,
    the housing having a central instruction surface on which the instruction manual is disposed, the first chamber hingedly connected to the central instruction surface on a first side, the second chamber hingedly connected to the central instruction surface on a second side, the housing configured to transition between an open configuration where the plurality of compartments are accessible for use and a closed configuration where the first chamber and the second chamber are each rotated relative to the central instruction surface and connected to one another to prevent access to the plurality of compartments.

* * * * *